(12) United States Patent
Sung et al.

(10) Patent No.: US 7,553,636 B2
(45) Date of Patent: *Jun. 30, 2009

(54) SURFACE EXPRESSION VECTORS HAVING PGSBCA THE GENE CODING POLY-GAMMA-GLUTAMATE SYNTHETASE, AND A METHOD FOR EXPRESSION OF TARGET PROTEIN AT THE SURFACE OF MICROORGANISM USING THE VECTOR

(75) Inventors: Moon-Hee Sung, Daejeon (KR);
Seung-Pyo Hong, Daejeon (KR);
Jong-Su Lee, Gyeonggi-do (KR);
Chang-Min Jung, Seoul (KR);
Chul-Joong Kim, Daejeon (KR); Kenji Soda, Kyoto (JP); Makoto Ashiuchi, Nankoku (JP)

(73) Assignees: Bioleaders Corporation (JP); M.D. Lab Co., Ltd., Department of Veterinary Science Chung Nam University (KR)

( * ) Notice: Subject to any disclaimer, the term of this patent is extended or adjusted under 35 U.S.C. 154(b) by 351 days.

This patent is subject to a terminal disclaimer.

(21) Appl. No.: 10/484,605

(22) PCT Filed: Aug. 9, 2002

(86) PCT No.: PCT/KR02/01522

§ 371 (c)(1),
(2), (4) Date: Feb. 12, 2004

(87) PCT Pub. No.: WO03/014360

PCT Pub. Date: Feb. 20, 2003

(65) Prior Publication Data

US 2004/0253704 A1 Dec. 16, 2004

(30) Foreign Application Priority Data

Aug. 10, 2001 (KR) .......................... 2001-0048373

(51) Int. Cl.
*C12N 15/09* (2006.01)
*C12N 1/21* (2006.01)
*C12N 15/63* (2006.01)

(52) U.S. Cl. .................. 435/69.1; 435/320.1; 435/69.7; 435/252.3

(58) Field of Classification Search .................. None
See application file for complete search history.

(56) References Cited

U.S. PATENT DOCUMENTS 5,356,797 A   10/1994   Niesel et al.

FOREIGN PATENT DOCUMENTS

| EP | 0 603 672 | * 12/1993 |
|----|-----------|-----------|
| JP | 2001-017182 | 1/2001 |
| WO | WO 93/10214 | 5/1993 |
| WO | WO 93/24636 | 12/1993 |
| WO | WO 94/10330 | 5/1994 |
| WO | WO 95/04069 | 2/1995 |
| WO | WO 95/04079 | 2/1995 |

OTHER PUBLICATIONS

Charbit, et al., J. Immunol., 139:1658-1664, 1987.
Agterberg, et al., Vaccine, 8:85-91, 1990.
Jung, et al., Nat. Biotechnol., 16:576-580, 1998.
Jung, et al., Enzyme Microb. Technol., 22:348-354, 1998.
Lee, et al., Nature Biotechnol., 18:645-648, 2000.
Francisco, et al., Proc. Natl. Acad. Sci. USA, 89:2713-2717, 1992.
Felici, et al., J. Mol. Biol., 222:301-310, 1991.
Fuchs, et al., Bio/Technology, 9:1369-1372, 1991.
Kornacker, et al., Mol. Microbiol., 4:1101-1109, 1990.
Klauser, et al., EMBO J., 9:1991-1999, 1990.
Newton, et al., Science, 244-70-72, 1989.
Hedegaard, et al., Gene, 85:115-124, 1989.
Samuelson, et al., J. Bacteriol., 177:1470-1476, 1995.
Ko, et al., Biotech, Bioeng., 57:430-437, 1998.
Makino, et al., J. Bacteriol., 171:722-730, 1989.
Ashiuchi, et al., Biochem. Biophy. Research Comm., 263:6-12, 1999.

* cited by examiner

*Primary Examiner*—Nancy Vogel
(74) *Attorney, Agent, or Firm*—Kelly K. Reynolds; Steven J. Hultquist; Intellectual Property/Technology Law

(57) ABSTRACT

The present invention relates to a surface expression vector having pgsBCA, a gene coding poly-gamma-glutamate synthetase and a method for expression of target protein at the surface of microorganism using the vector. The vector, in which foreign genes are inserted, transforms microorganisms and makes foreign proteins expressed stably on the surface of microorganisms.

11 Claims, 23 Drawing Sheets

FIG. 1
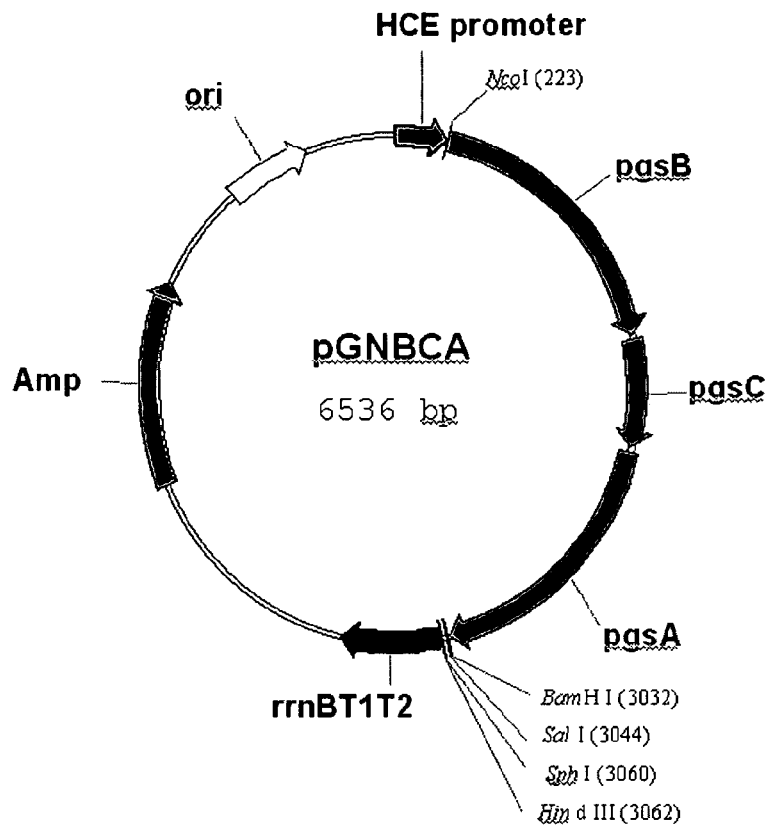
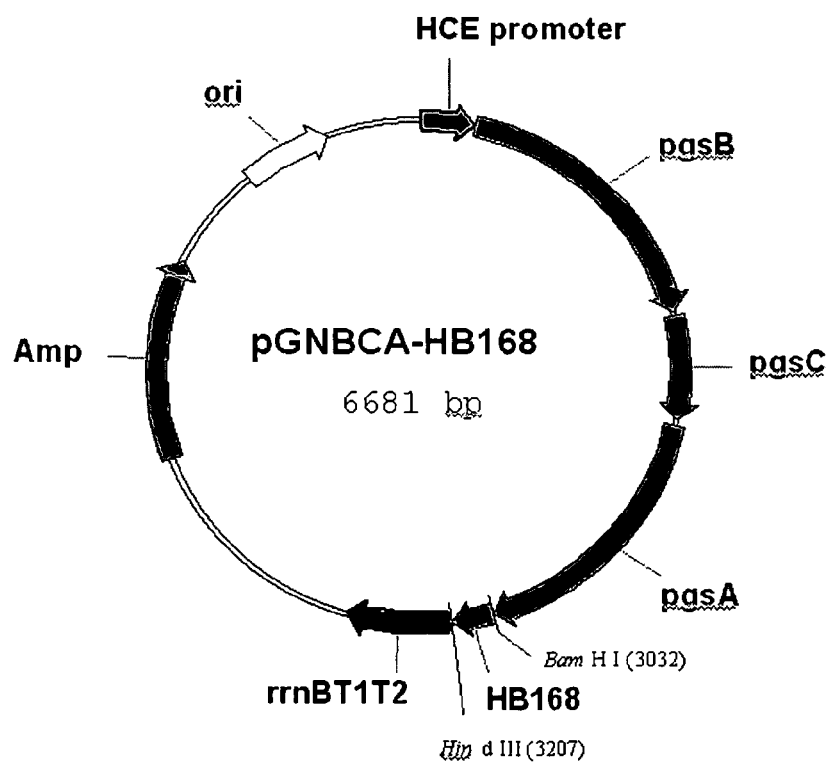

FIG. 2
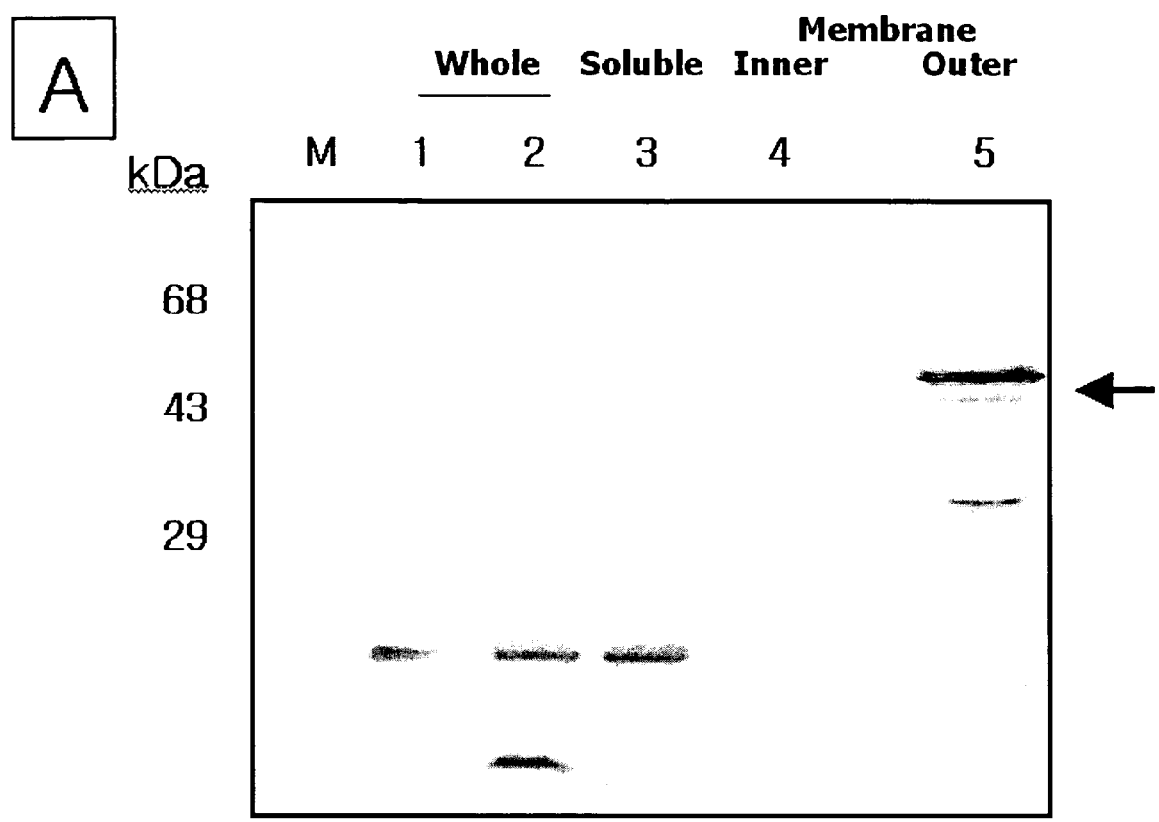
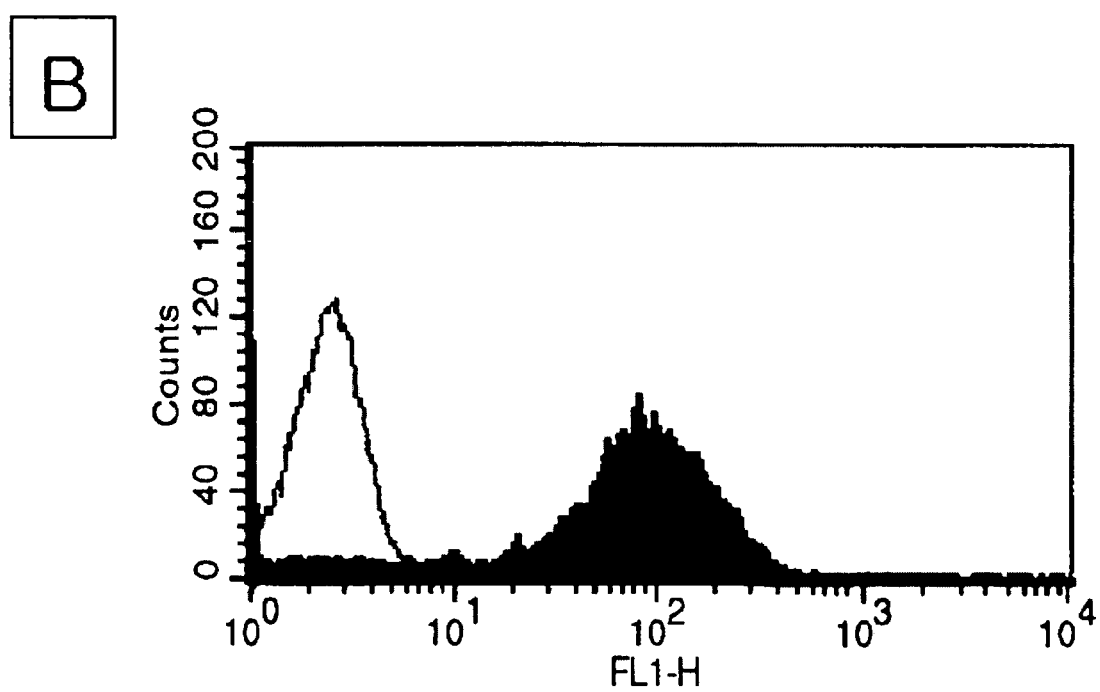

FIG. 3
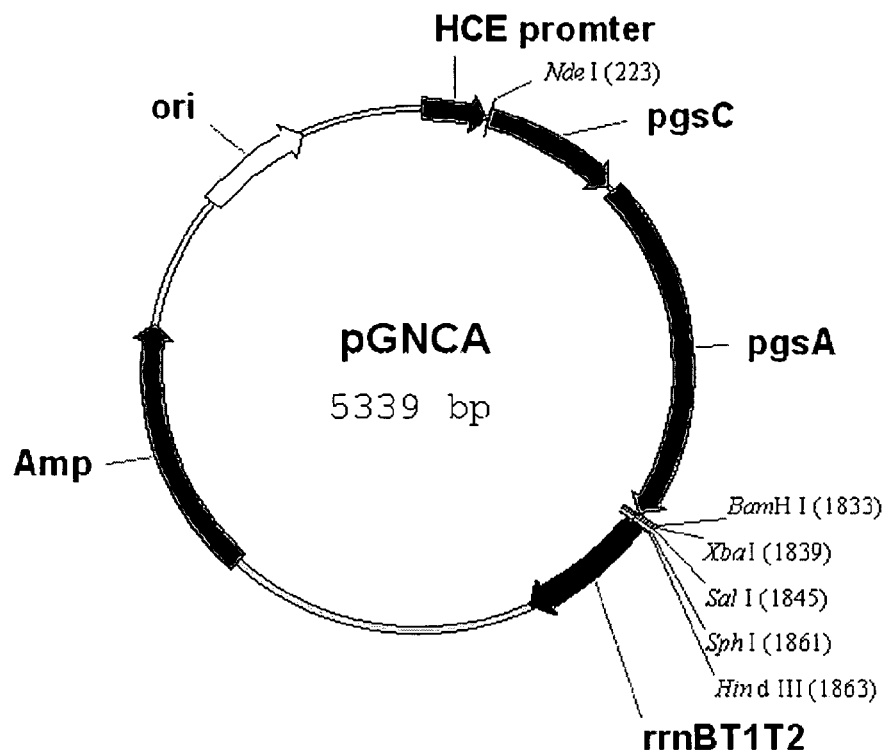
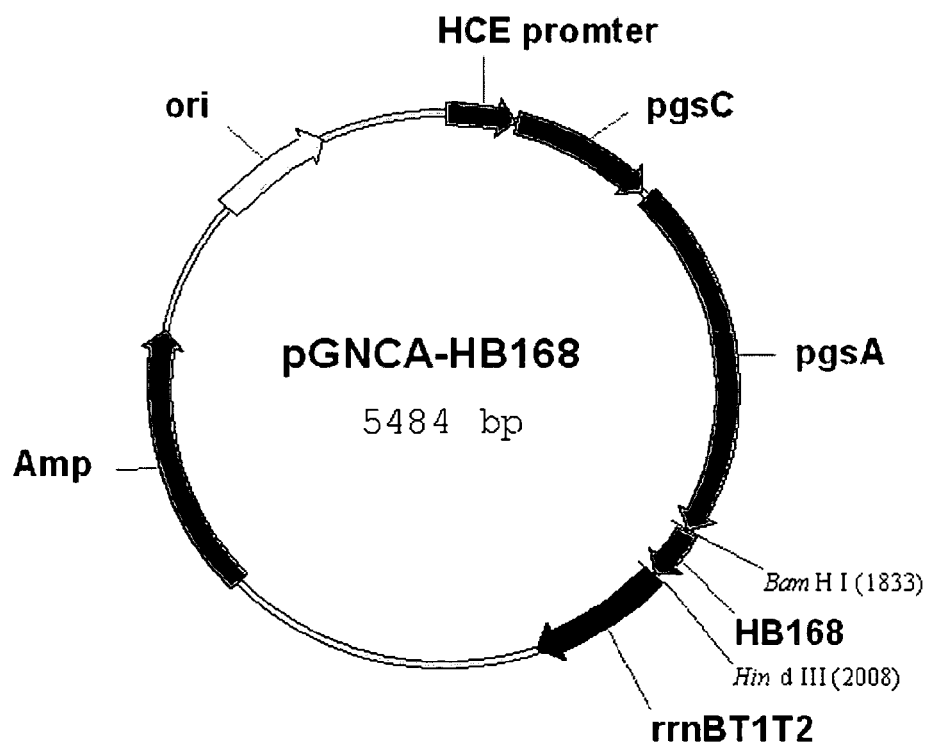

FIG. 4
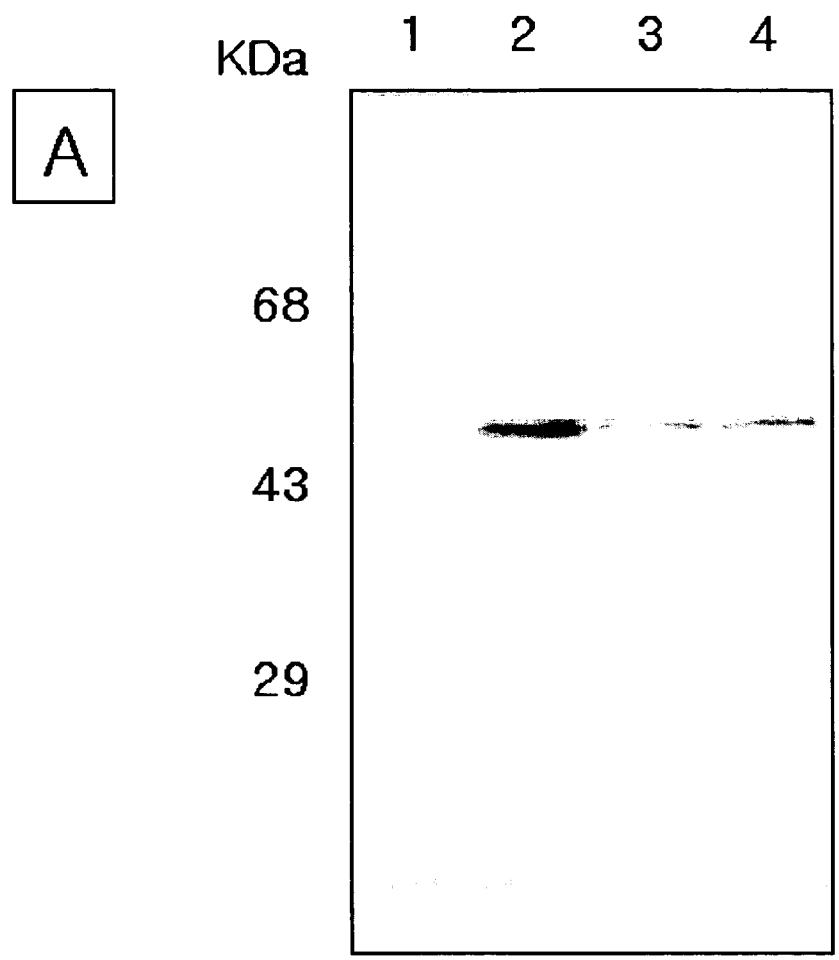
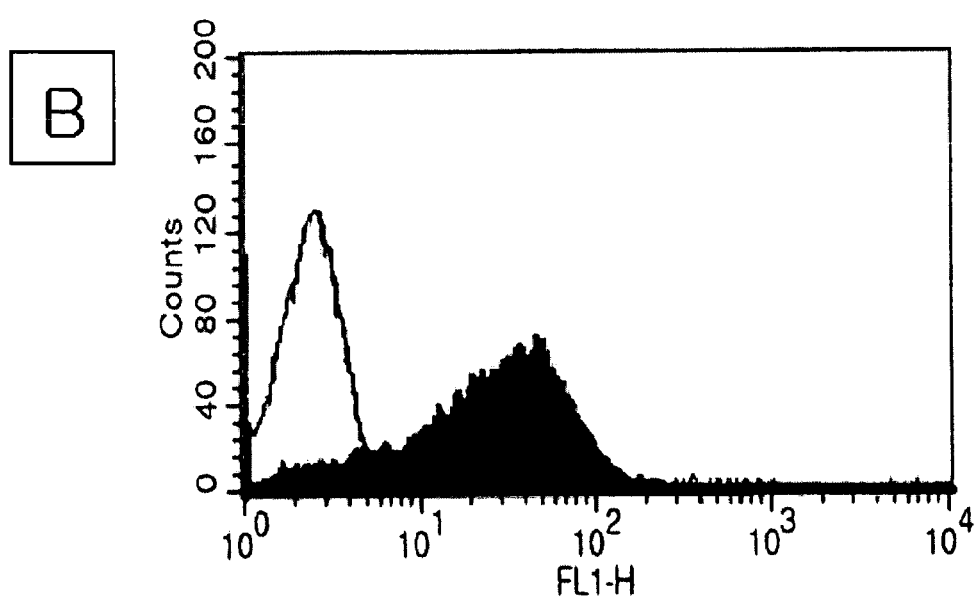

FIG. 5
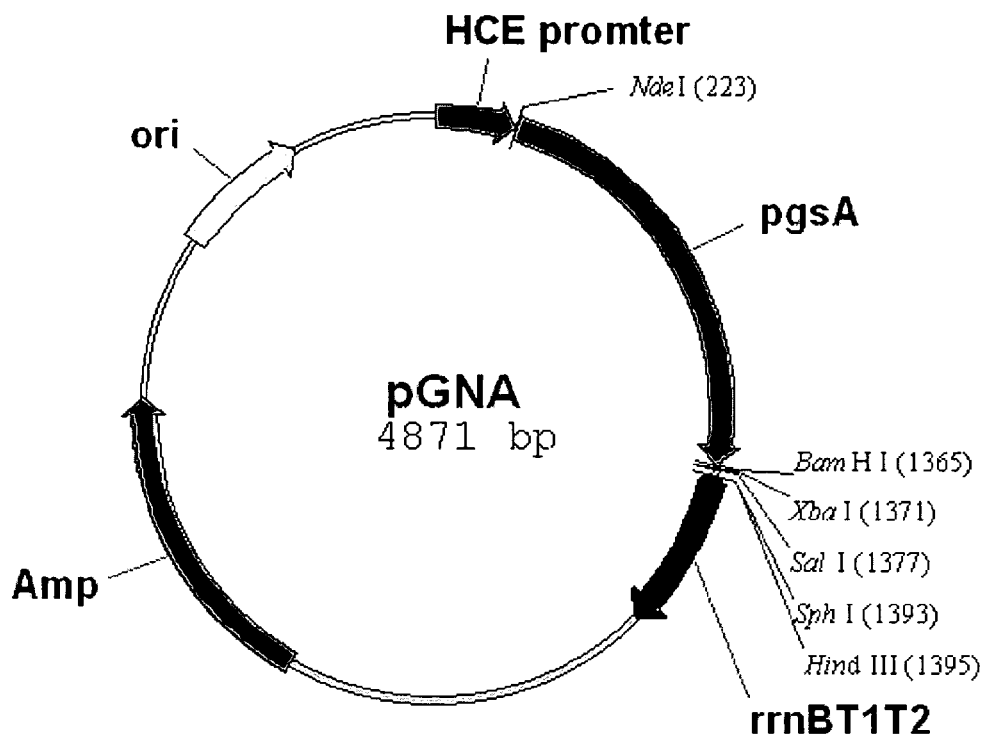
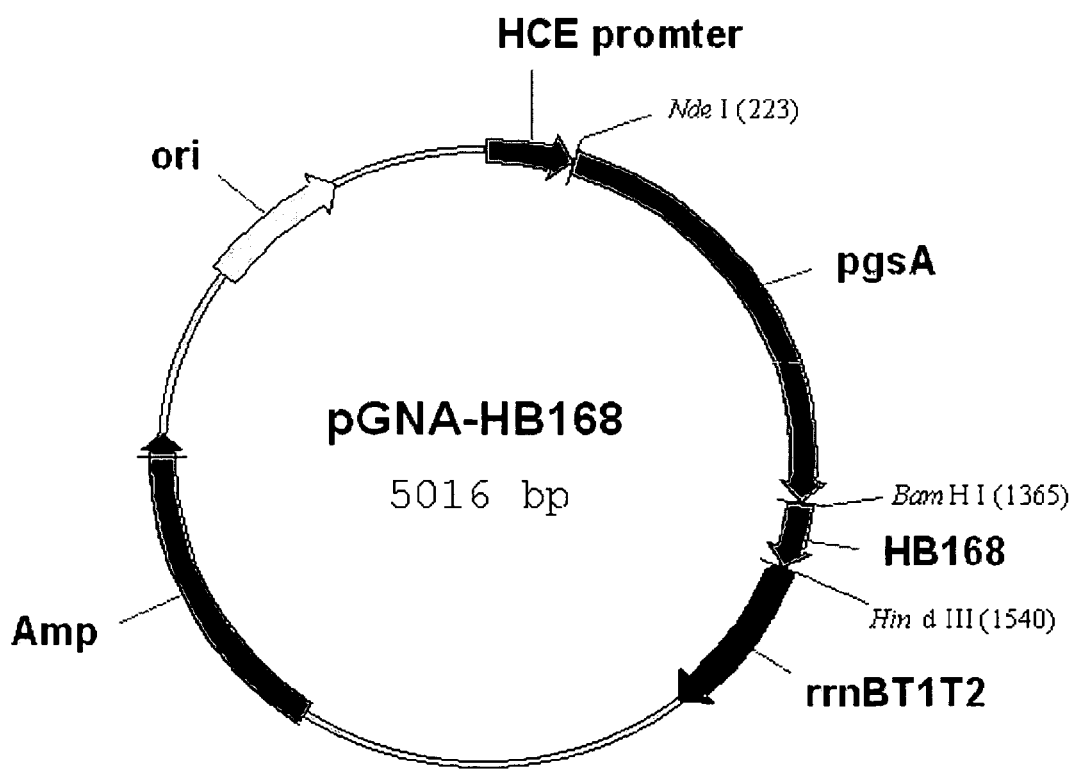

FIG. 6
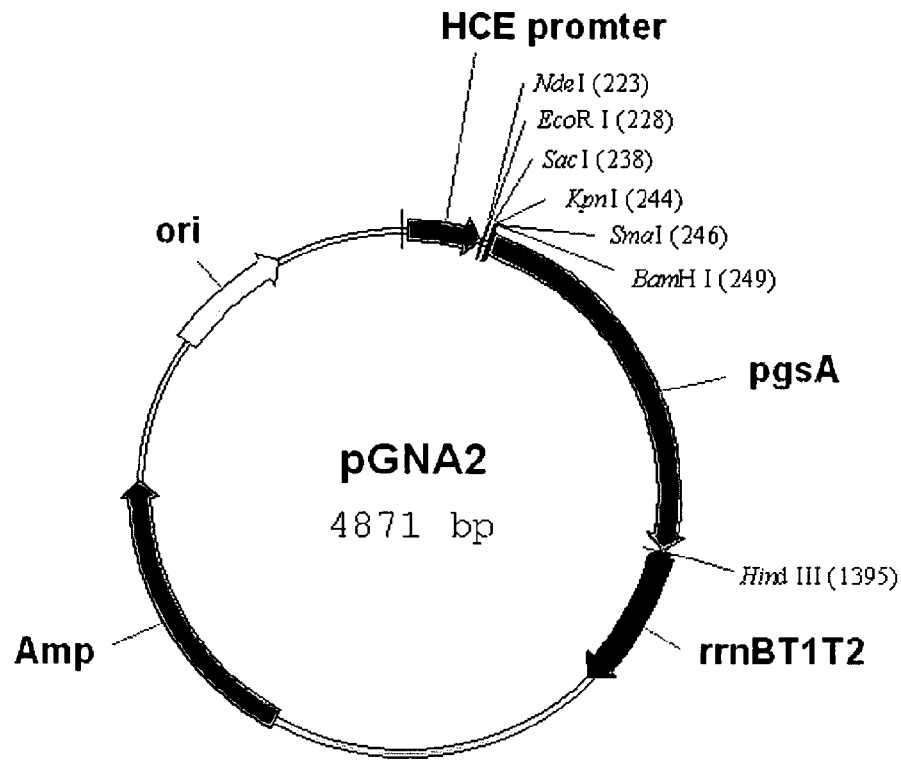
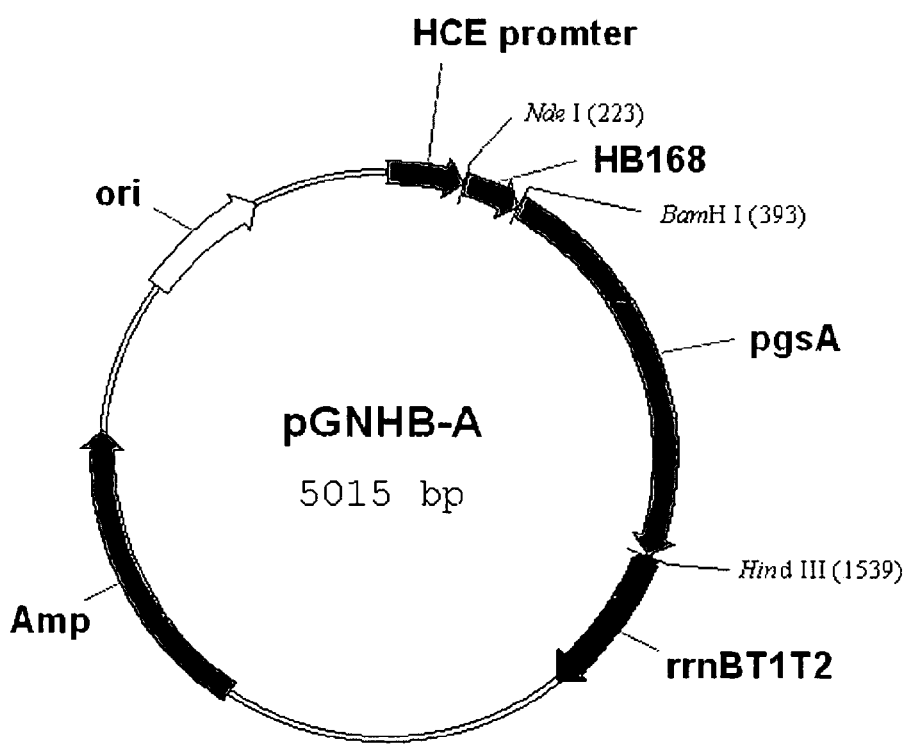

FIG. 7
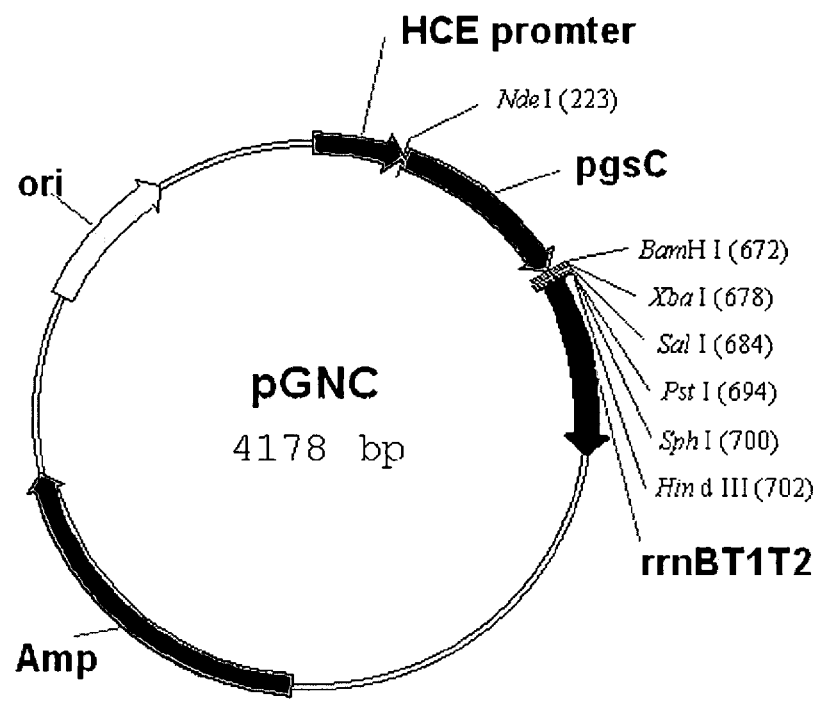
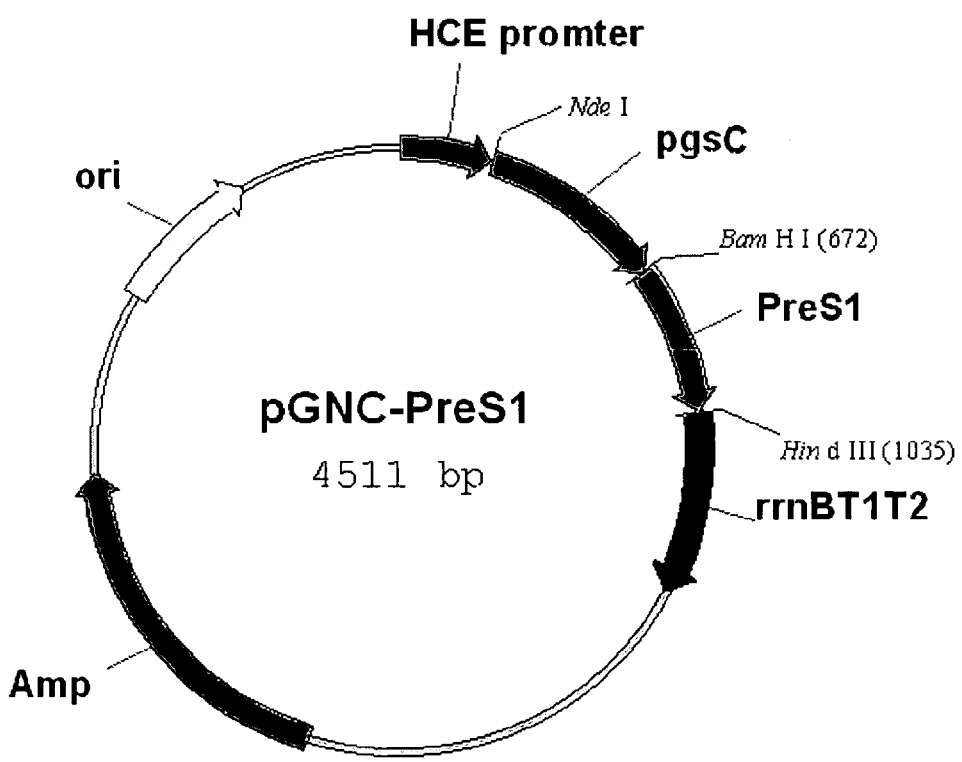

FIG. 9
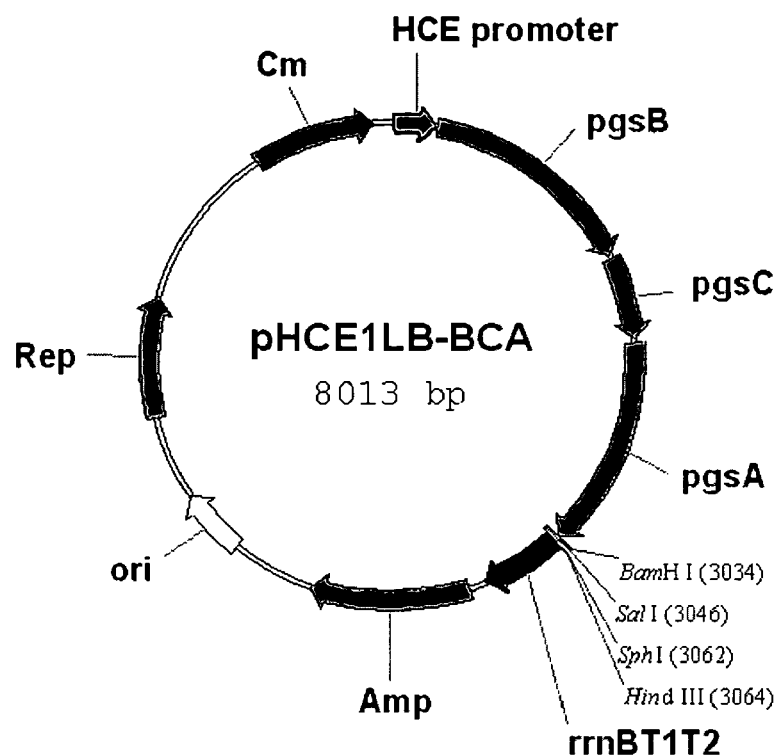
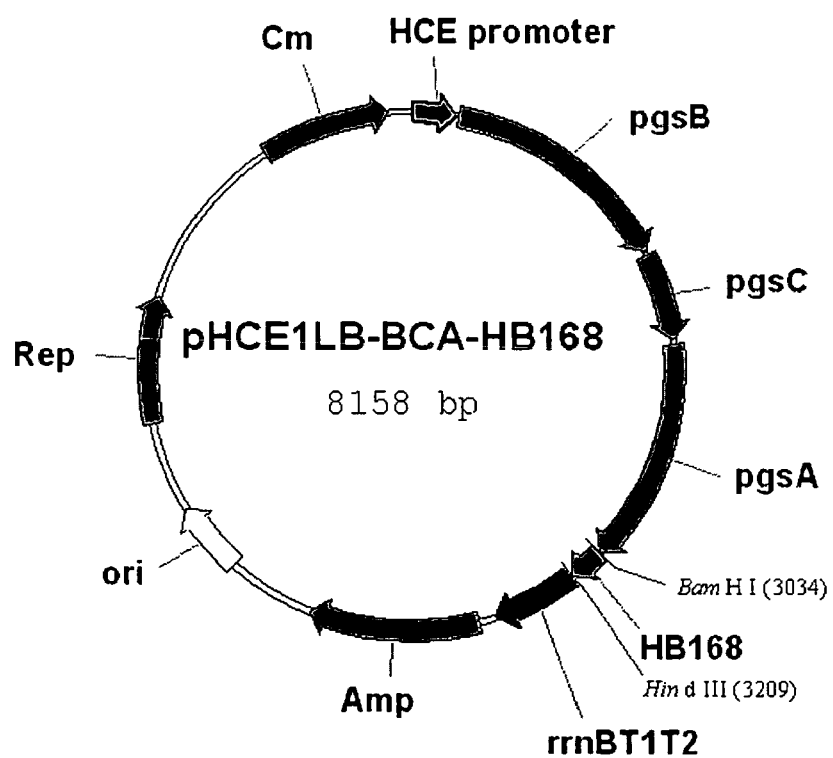

FIG. 11
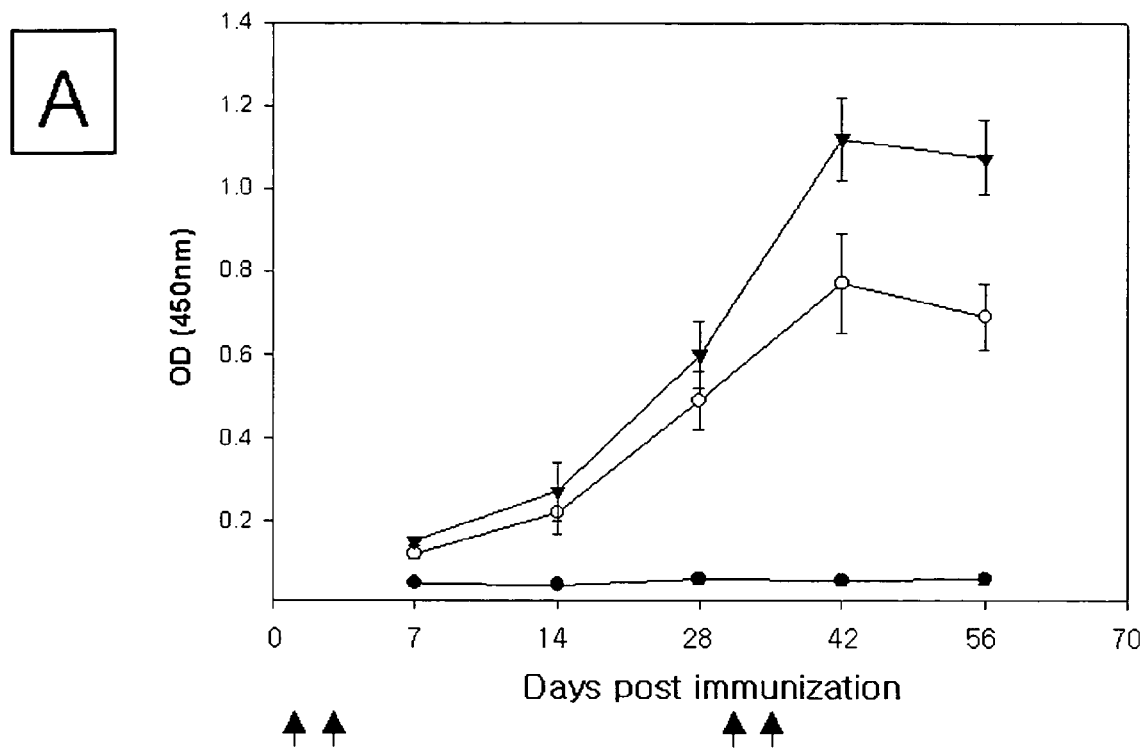
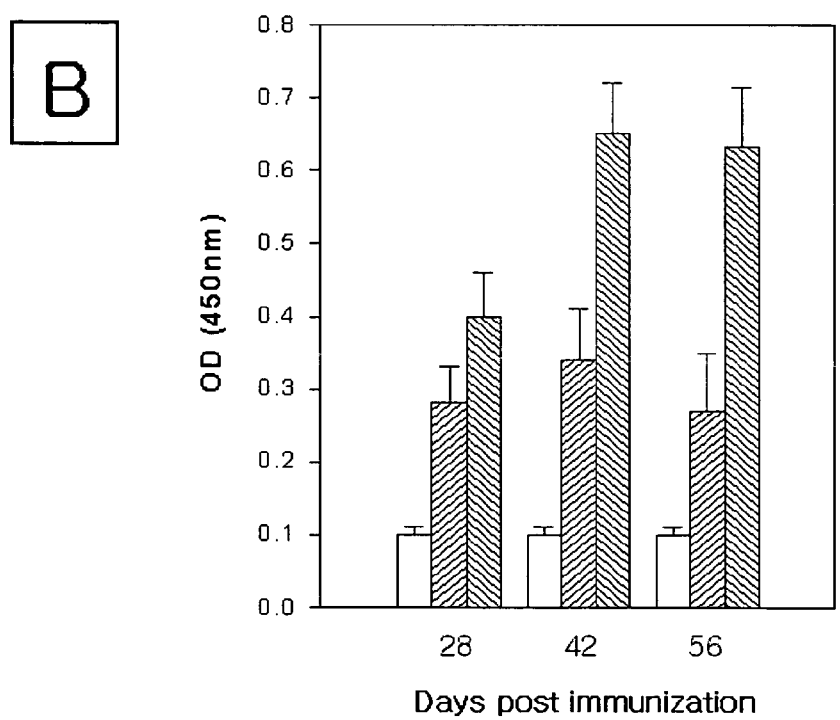

FIG. 12
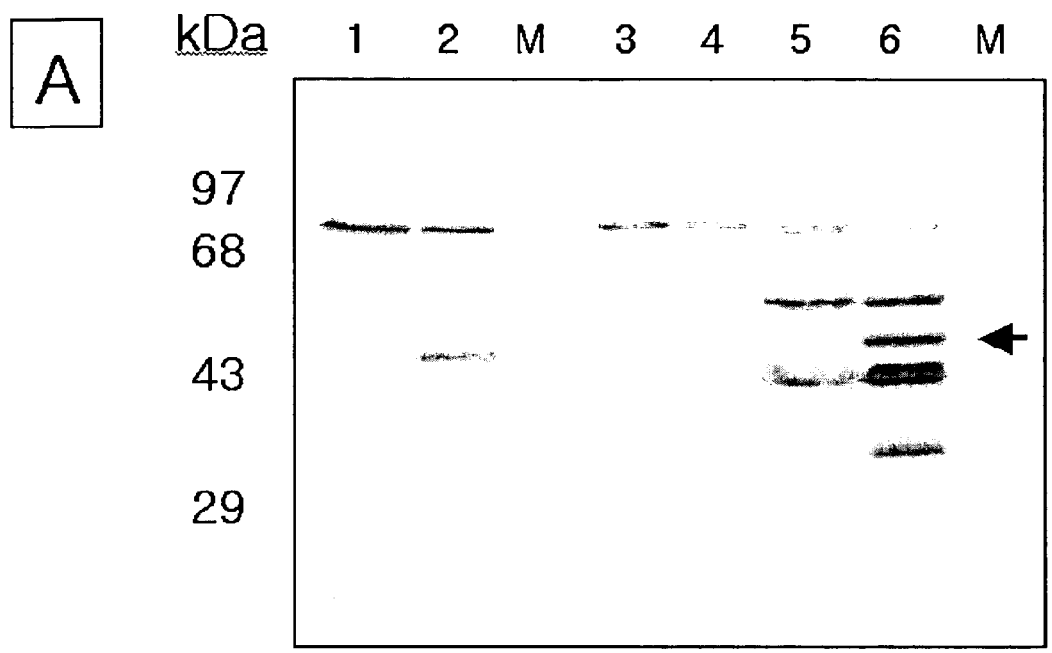
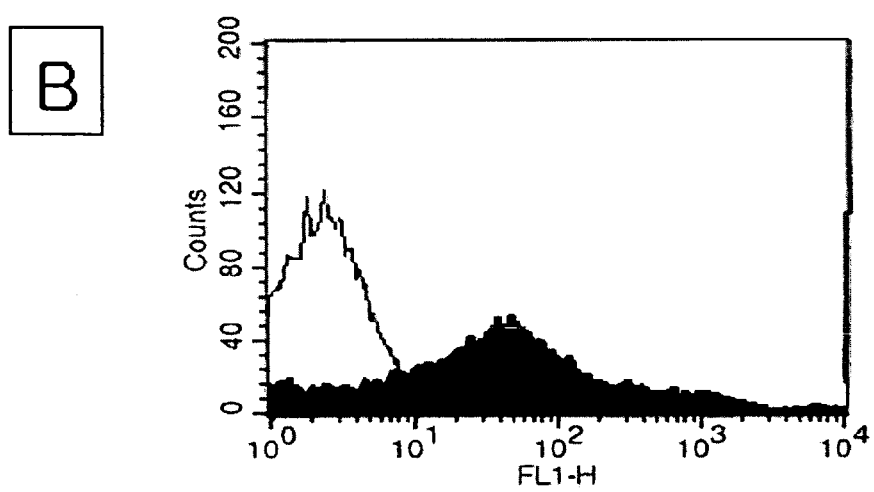

FIG. 13
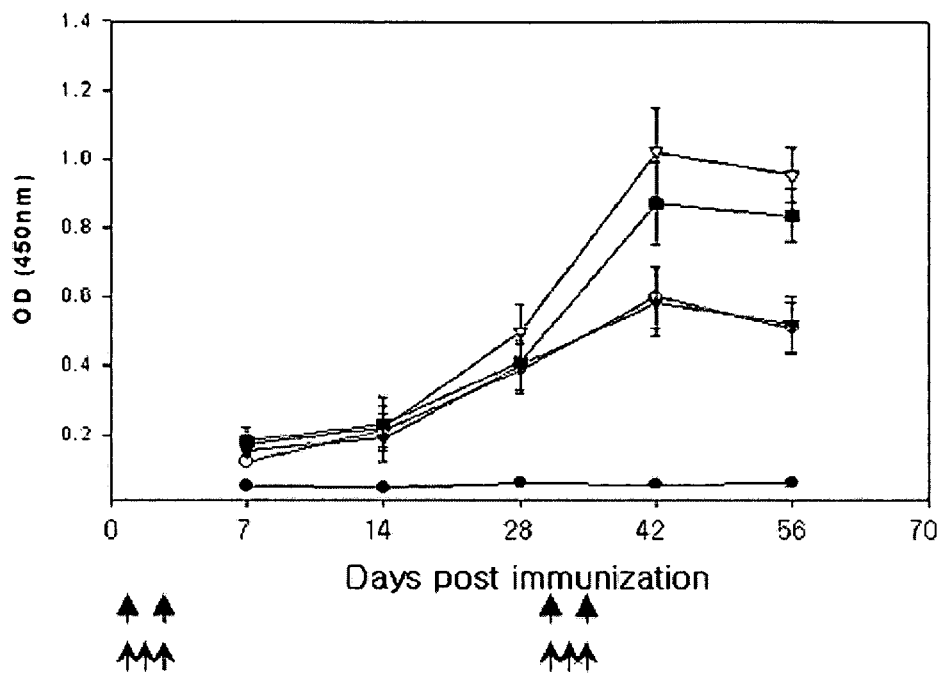
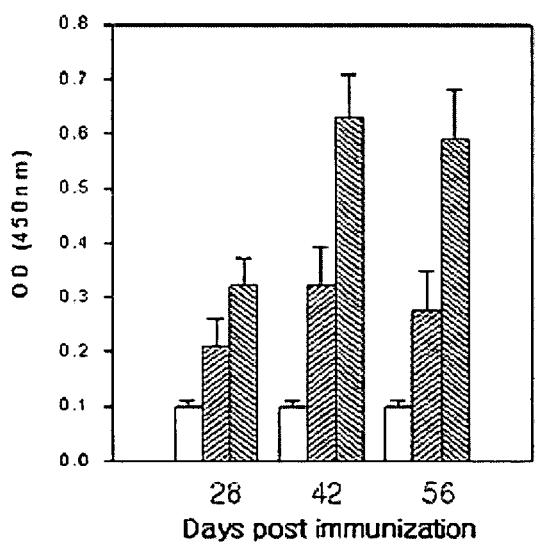
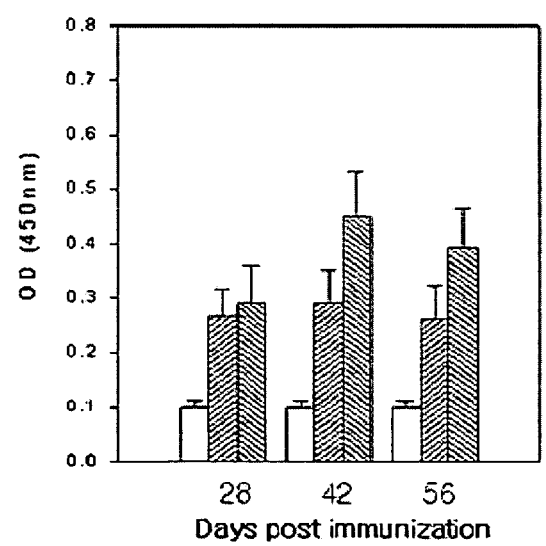
nasal administered　　　　　　oral administered FIG. 14
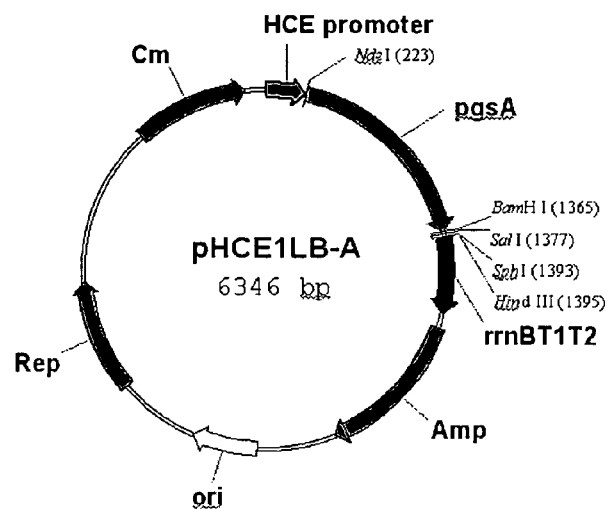
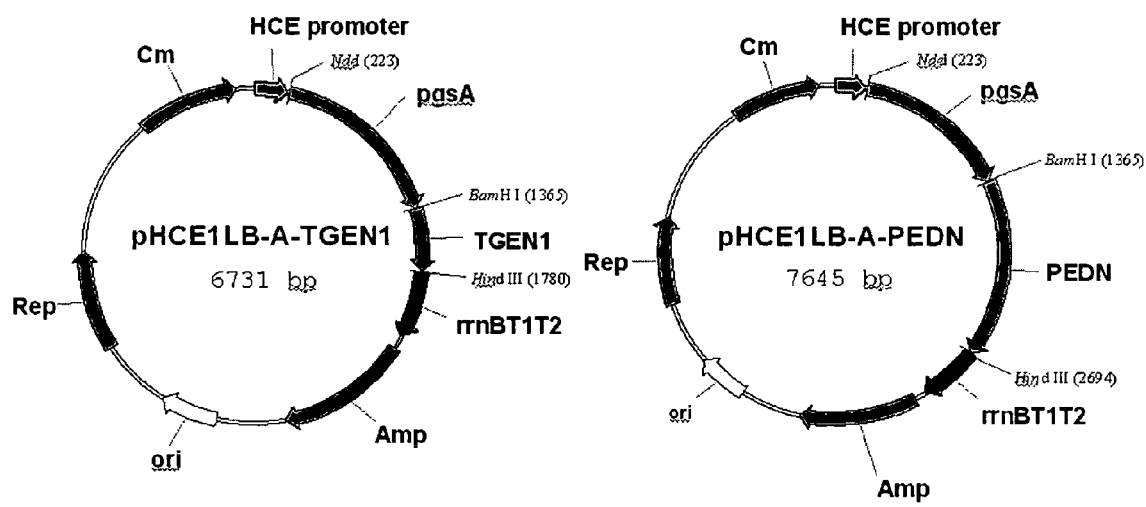

FIG. 15
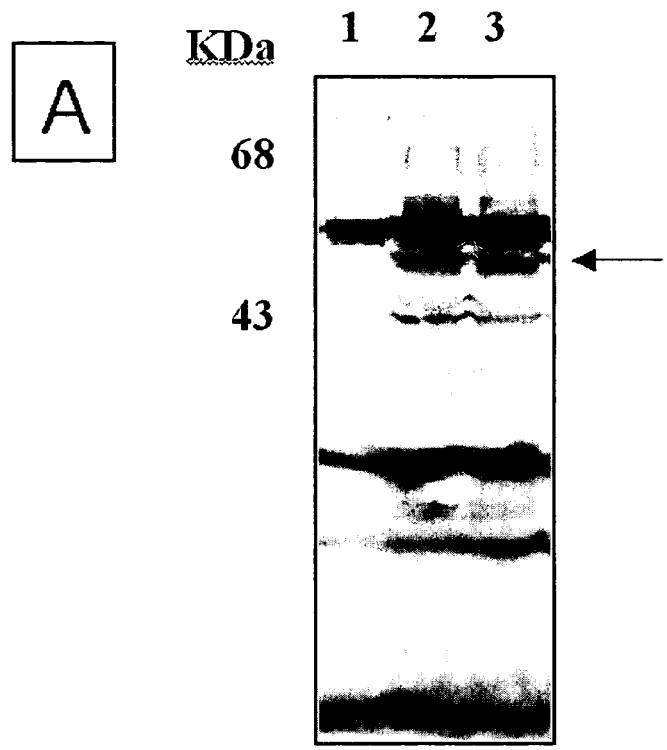
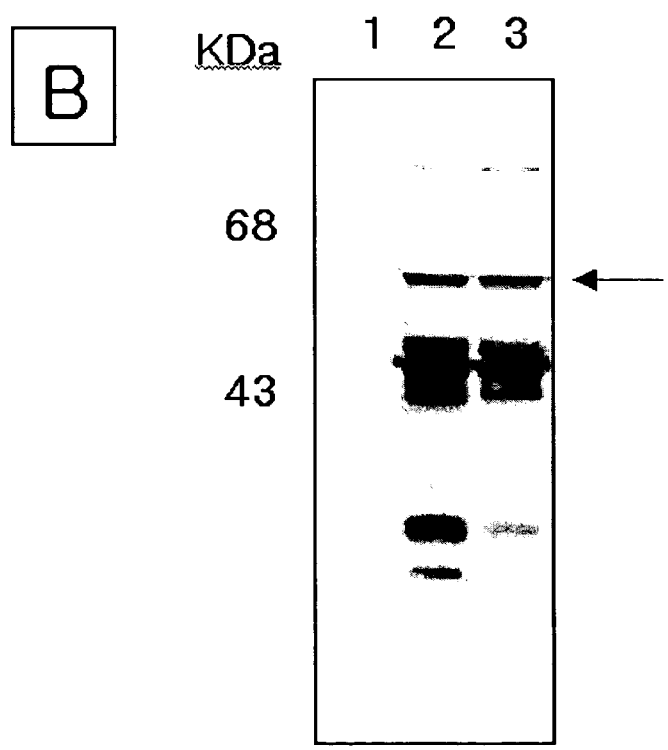

FIG. 16
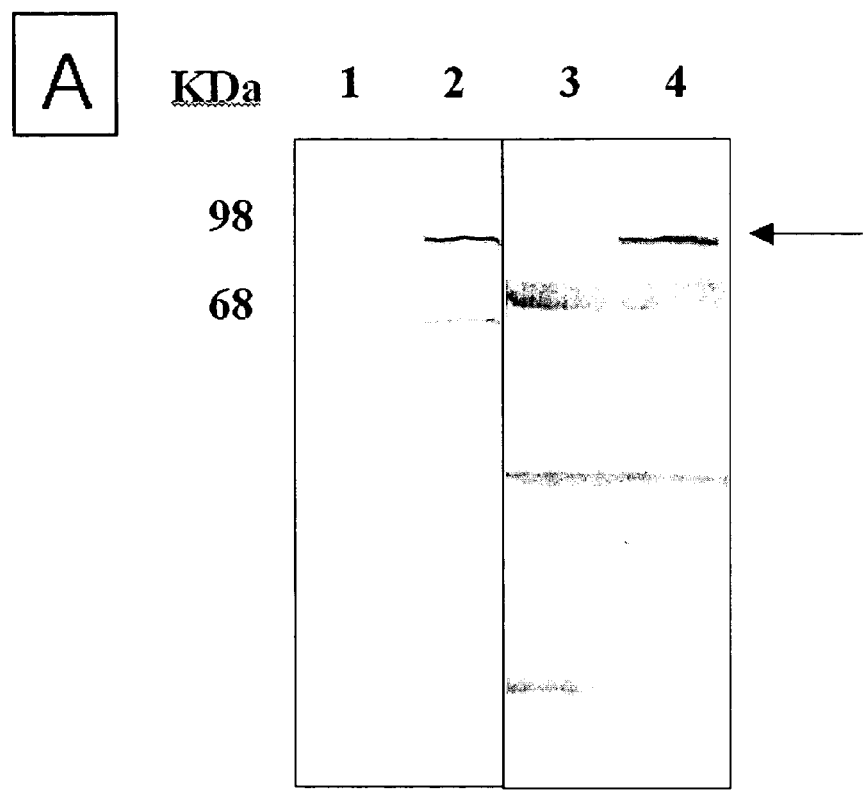
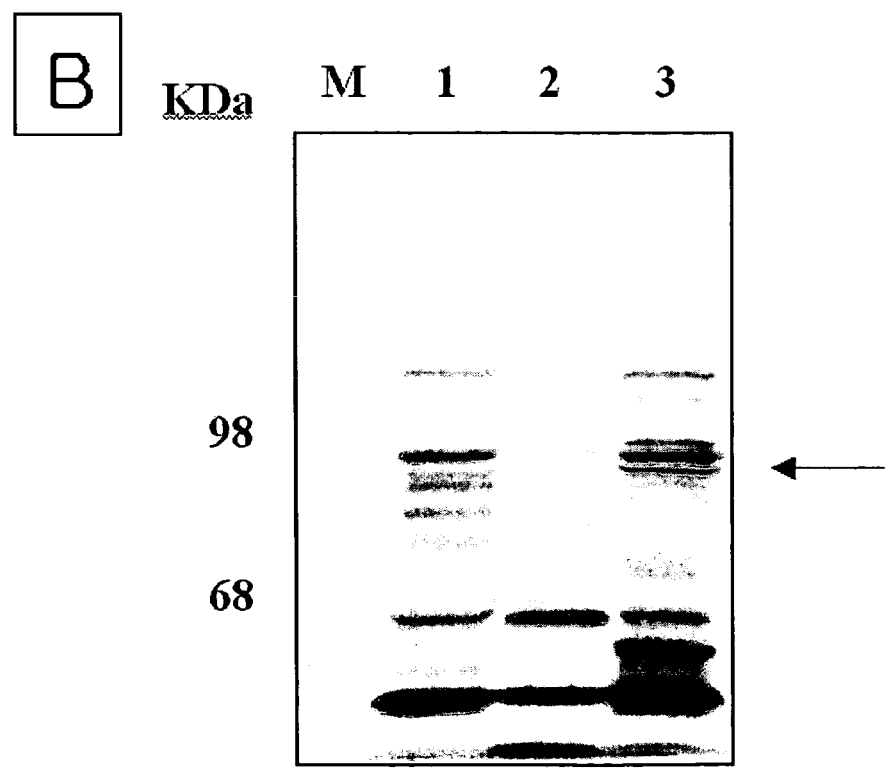

FIG. 17
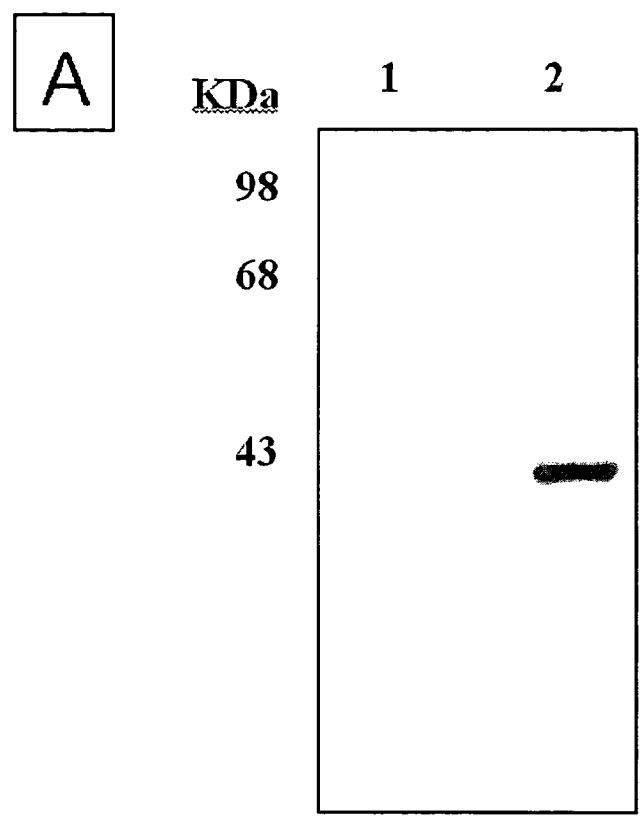
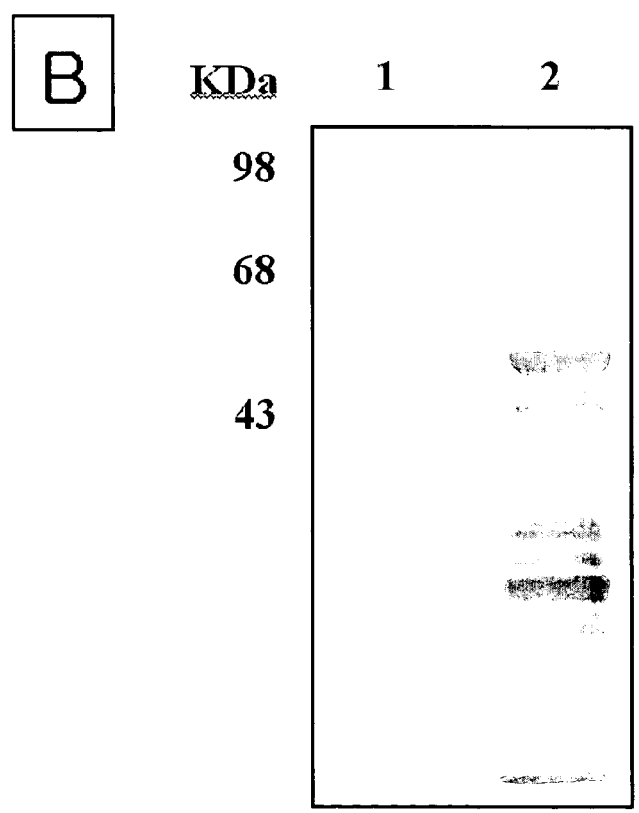

FIG. 18
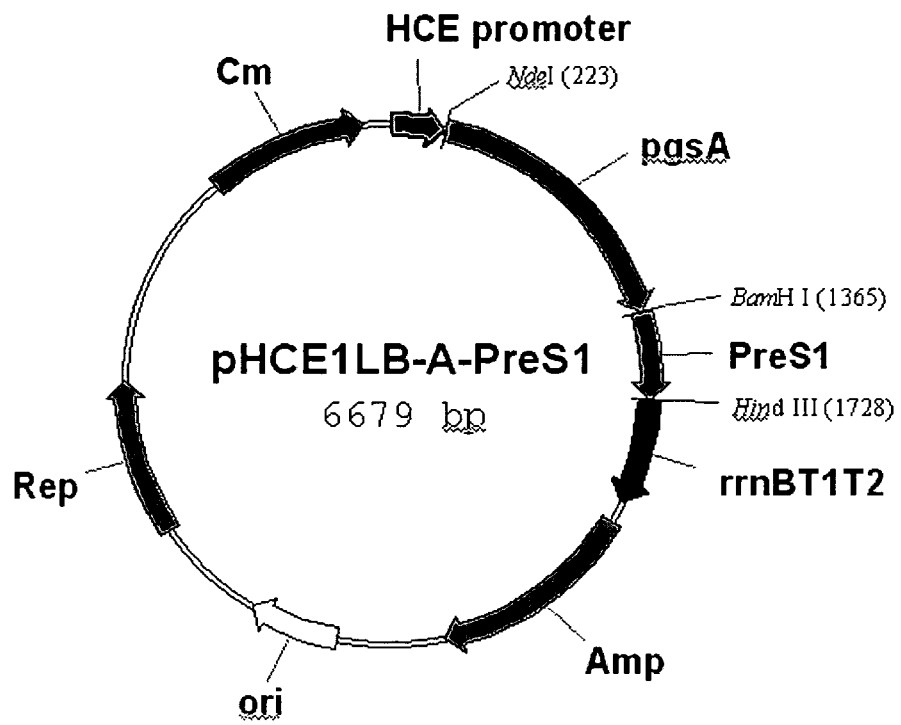
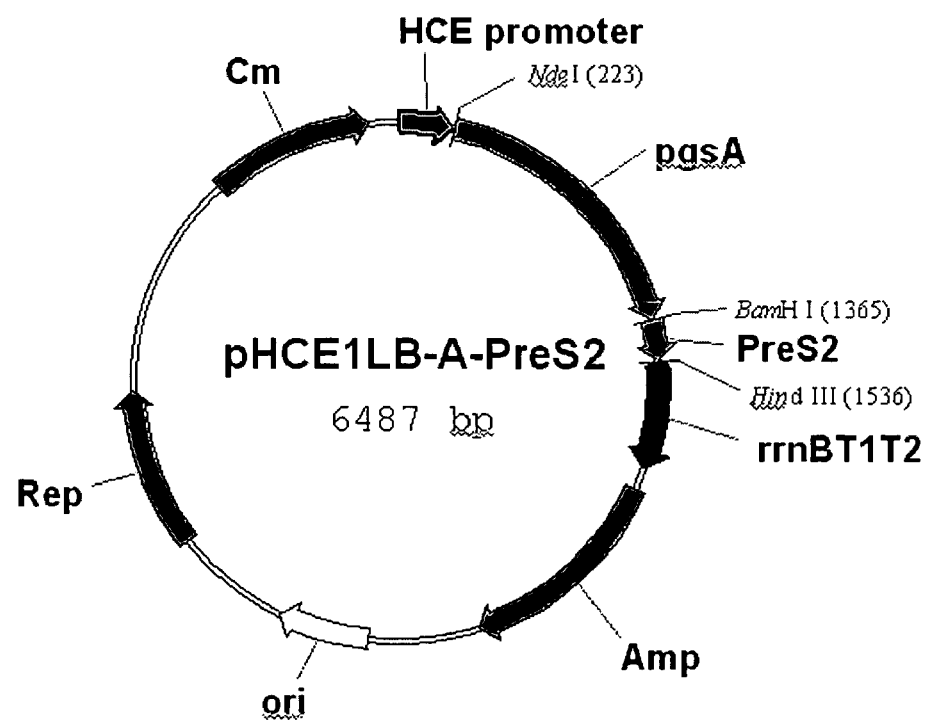

FIG. 19
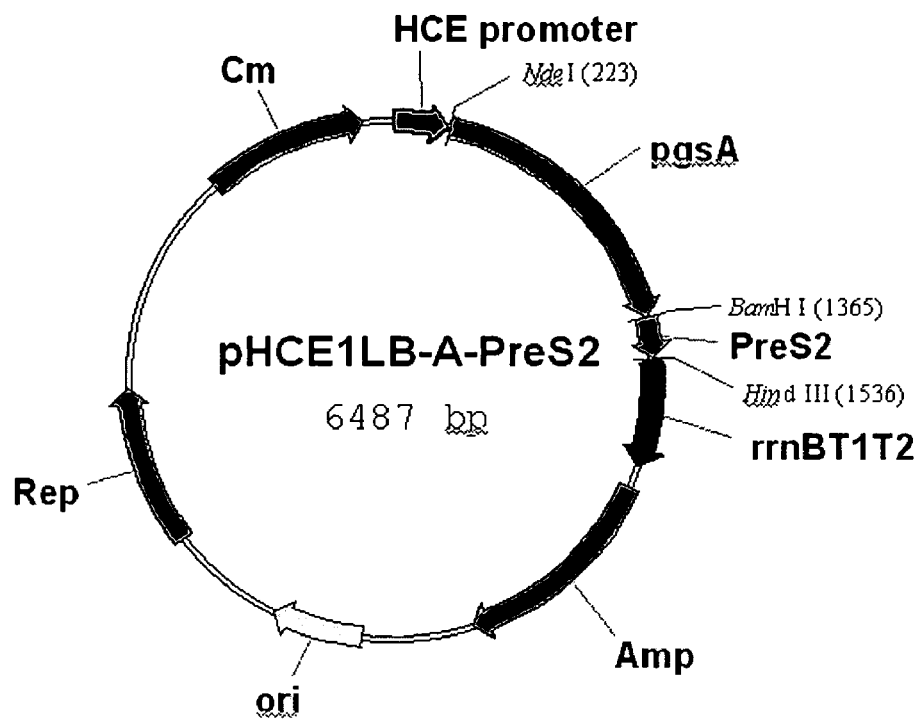
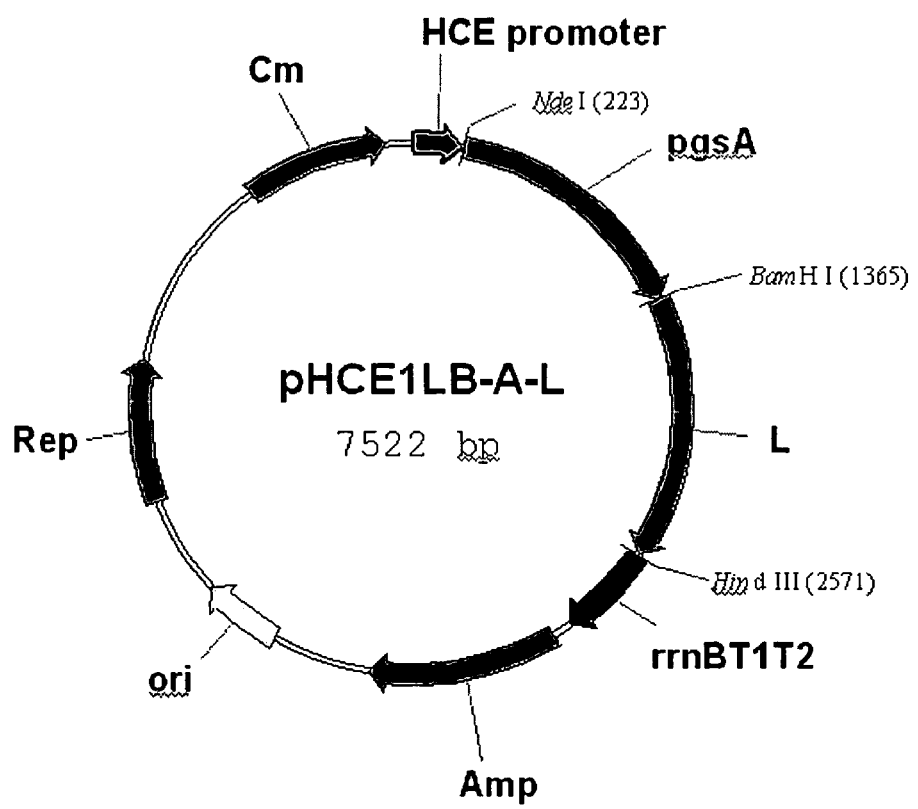

FIG. 20
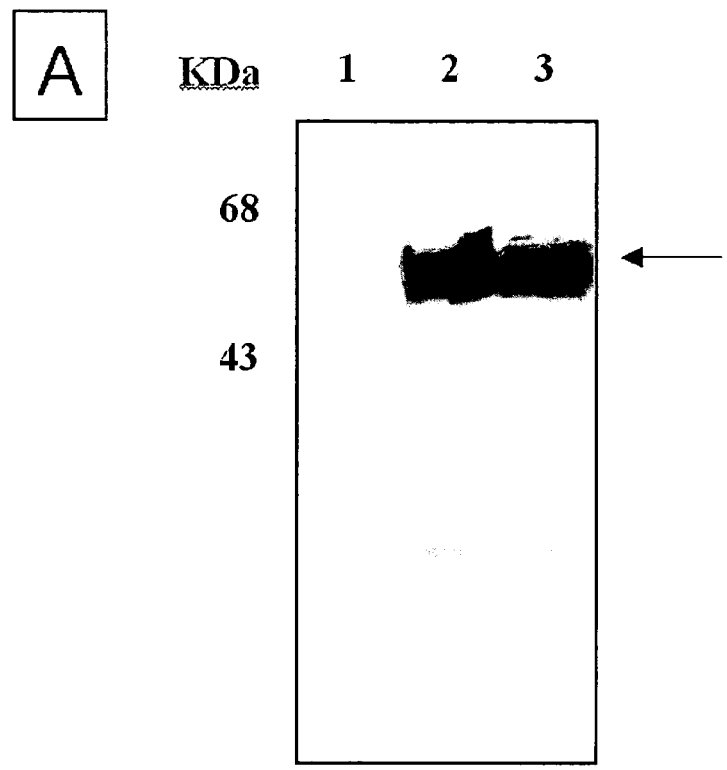
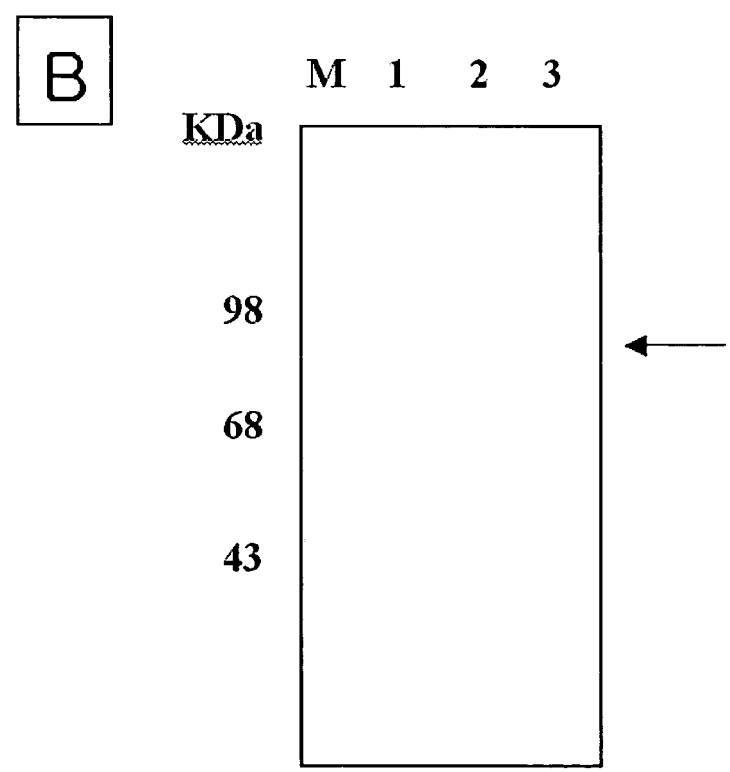

FIG. 22
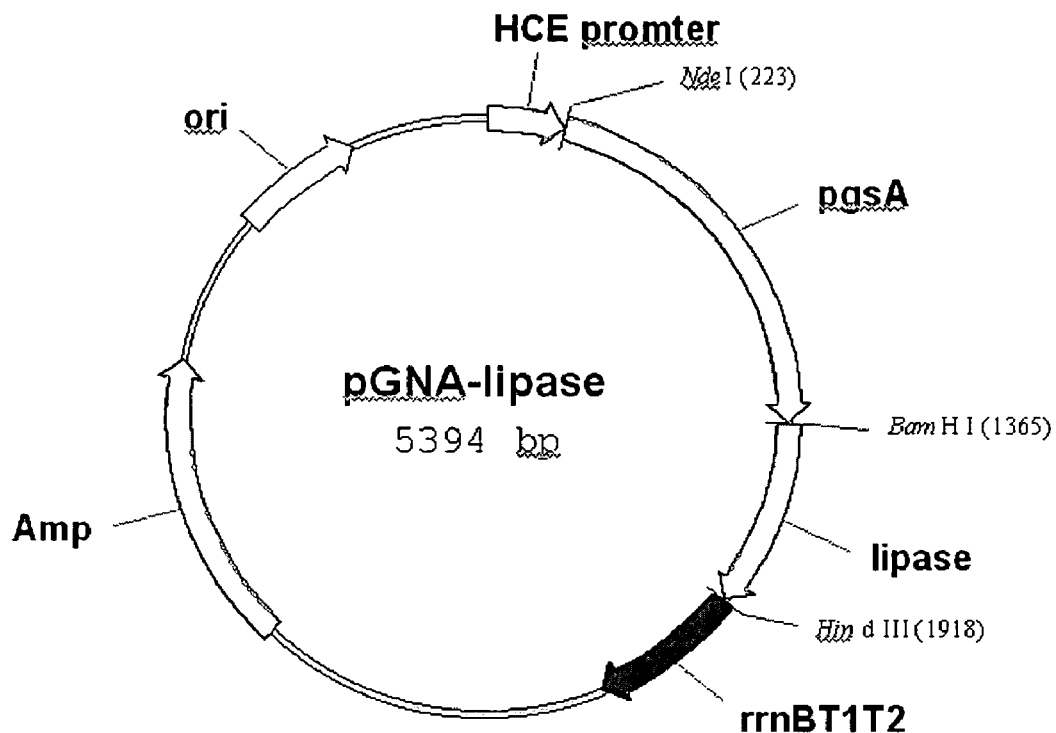
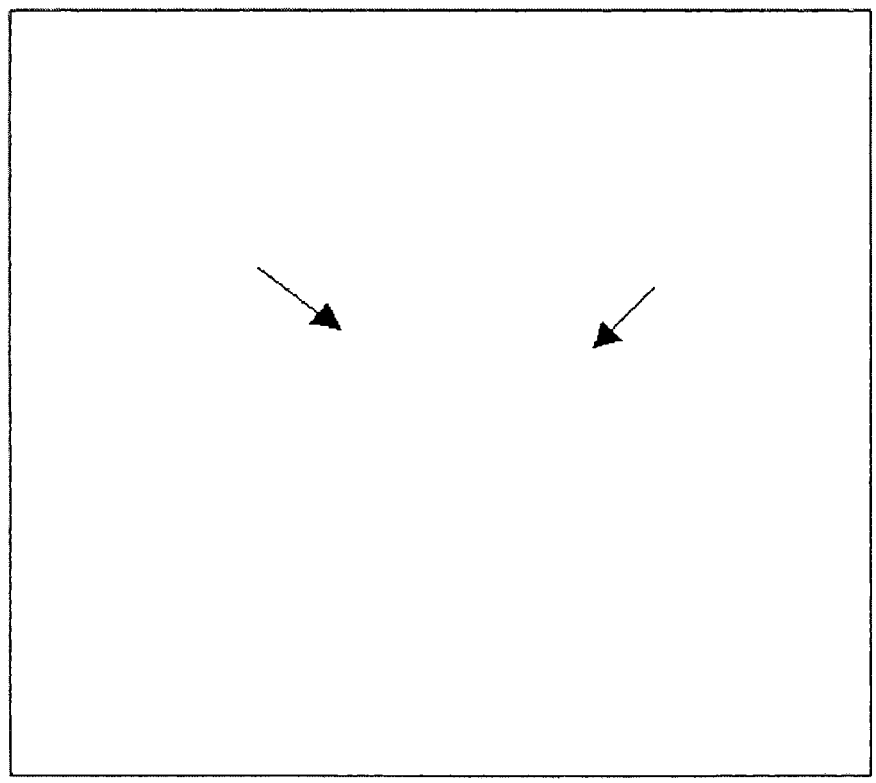

FIG. 23
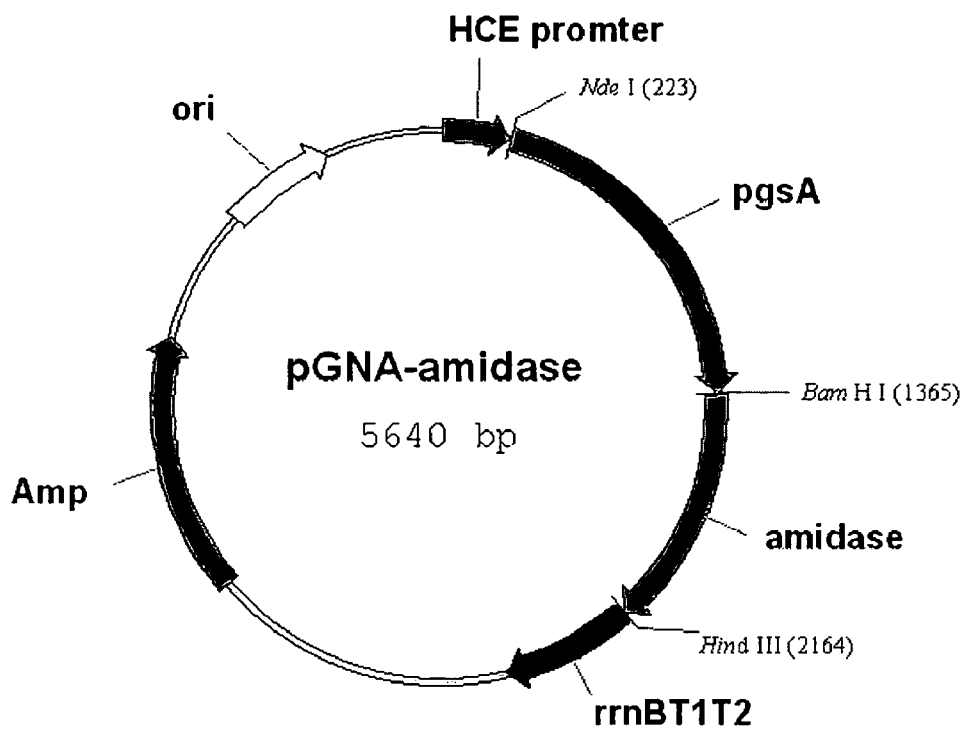
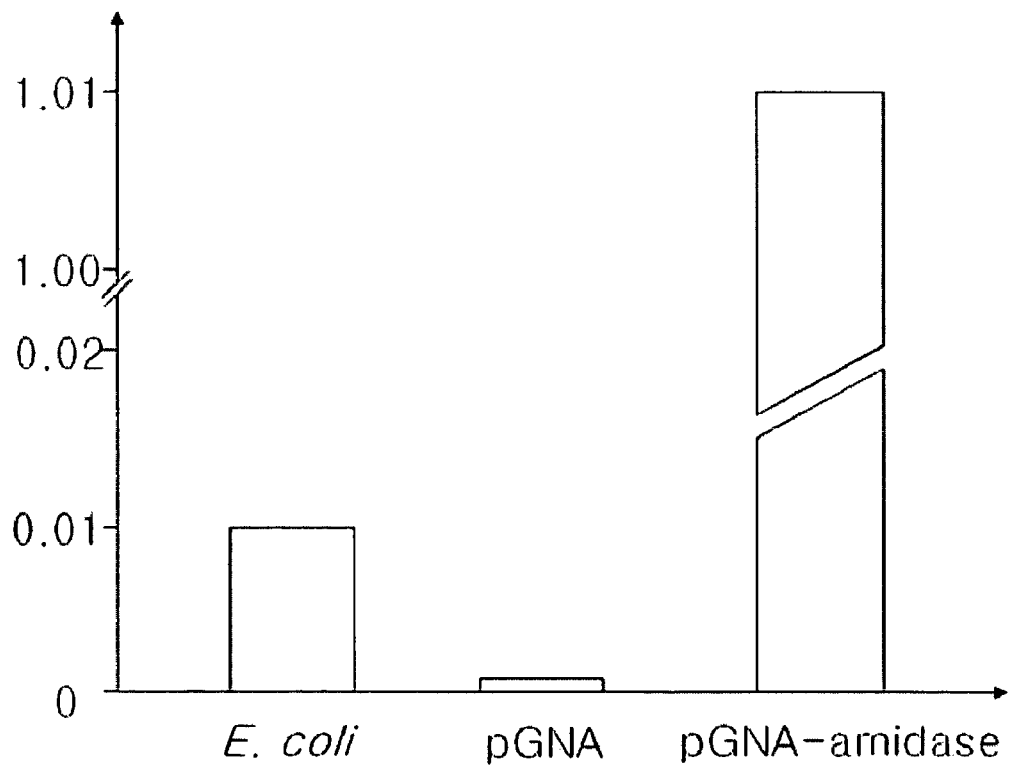

SURFACE EXPRESSION VECTORS HAVING PGSBCA THE GENE CODING POLY-GAMMA-GLUTAMATE SYNTHETASE, AND A METHOD FOR EXPRESSION OF TARGET PROTEIN AT THE SURFACE OF MICROORGANISM USING THE VECTOR

STATEMENT OF JOINT RESEARCH AGREEMENT

This invention was made as a result of activities undertaken within the scope of a joint research agreement between the following parties: Bioleaders Corp.; Korea Research Institute of Bioscience and Biotechnology; Chosun University; Genolac BL Corp.; Imbio Corp.; M.D. Lab Co., Ltd.; and Bioleaders Japan Corp.

CROSS-REFERENCE TO RELATED APPLICATIONS

This application is filed under the provisions of 35 U.S.C. §371 and claims the priority of International Patent Application No. PCT/KR02/01522 filed Aug. 9, 2002, which in turn claims priority of Korean Patent Application No. 2001-48373 filed Aug. 10, 2001.

TECHNICAL FIELD

The current invention relates to novel expression vectors that can efficiently produce exogenous proteins on a microbial surface and exploit the cell outer membrane protein (pgsBCA) participating in the synthesis of poly-γ-glutamate derived from a *Bacillus* sp. strain. In addition, the present invention relates to a method for expressing an exogenous protein on a microbial surface by exploiting the cell outer membrane protein (pgsBCA) participating in the synthesis of poly-γ-glutamate derived from a *Bacillus* sp. strain.

BACKGROUND ART

Recently, the use of surface expression to produce valuable exogenous proteins on cell surfaces has been attempted with bacteriophages, bacteria, and yeast for the purpose of creating new vaccines, screening various kinds of antigens and antibodies, and fixing useful enzymes onto cell surfaces.

Originally, the idea of expressing exogenous proteins on a cell surface was to produce antigenic regions of peptides, especially for the large-scale stable expression of vaccines. Currently, pathogenic bacteria are randomly mutated to produce vaccines and screened to collect bacteria with consistent and stable titers. However, unfortunately, the enzymatic activity is invariably lost after oral administration to humans and animals. Therefore, many studies have been conducted to over come this problem. Normally, the cell surface protein of a Gram-negative bacterium is adopted and its gene ligated with an antigenic protein gene, which is then introduced to proper host cells so that fusion proteins are efficiently produced on the cell surface. The recombinant protein prepared through this procedure can be an effective antigen as it is protruded onto the cell surface. In particular, Gram-negative bacteria have been reported as most suitable for production, as the lipopolysaccharides (LPS) in the cell outer membrane enhance the antigenicity of the proteins expressed on the cell surface.

To express exogenous proteins on a cell surface, the presence of a secretion signal is required within the primary sequence, since this passes the biosynthesized cell proteins through the cell membrane. Besides, in Gram-negative bacteria, the recombinant protein must also pass though the cell inner membrane and space between the cell membranes, be inserted and attached to the cell outer membrane, and finally stably protruded to the external side of the cell membrane.

Practically, there are certain proteins that include such a secretion signal and targeting signal and are stably protruded onto the cell surface, for example, cell surface proteins, specific enzymes, and toxin proteins. As such, if these secretion and targeting signals are associated with a proper promoter, exogenous proteins can be successfully expressed onto a bacterial surface.

In general, the cell surface proteins adopted for the surface expression of foreign proteins can be basically classified to 4 kinds, a cell outer membrane, lipoprotein, secretion protein, and cell surface organ protein. Until now, the surface proteins present in Gram-negative bacteria, for example, LamB, PhoE, and OmpA, have been mainly utilized to produce useful foreign proteins. However, these proteins present structural restrictions as regards the size of the insertable proteins, which are inserted into the protruded loop on the cell surface. Since the C- and N-termini of the inserted exogenous protein should be stereochemically close, if they are distant, connected peptides can be ligated to reduce the distance between the two termini.

Concretely, if LamB and PhoE are used to insert an exogenous polypeptide consisting of more than 50~60 amino acids, structural constraints are invoked preventing the creation of a stable protein on the cell membrane (Charbit, et al., J. Immunol., 139: 1658-1664, 1987; Agterberg, et al., Vaccine, 8: 85-91, 1990). Although OmpA can be utilized to introduce exogenous proteins into the protruded loop, only a partial fragment of OmpA containing a minimal targeting signal can actually be added due to the structural constraint. β-lactamase has been expressed on a cell surface by connecting the OmpA targeting signal at the C-terminus.

Recently, the ice-nucleation protein (INP) derived from *Pseudomonas* sp. was found to be a cell outer membrane of Gram-negative bacteria and utilized for surface expression (Jung et al., Nat. Biotechnol., 16: 576-580, 1998; Jung et al., Enzyme Microb. Technol., 22(5): 348-354, 1998; Lee et al., Nat. Biotechnol., 18: 645-648, 2000). Jung and colleagues expressed levansucrase onto a cell surface using the ice nucleation protein, consisting of the N-terminus, central repetitive region, and C-terminus, and ligating the levansucrase gene at the C-terminus, while also expressing carboxymethylcellulase using the ice nucleation protein, consisting of the N-terminus, deleted central repetitive region, and C-terminus, and fusing the gene at the C-terminus, so as to assay the respective enzymatic activities. In addition, Lee and colleagues used the ice-nucleation protein, comprising of just the N-terminus or the N-terminus and C-terminus, ligated with the hepatitis B virus surface antigen and hepatitis C virus core antigen at each terminus, for expression on the cell surface of an *Escherichia coli* or *Salmonella typhi* Ty21a strain, then confirmed that these proteins were effective for complex live vaccines.

Lipoproteins have also been utilized as a surface protein for surface expression. In particular, *E. coli* lipoproteins can pass through the cell inner membrane based on the secretion signal at the N-terminus and contain L-cystein at the terminus directly connected to the cell outer membrane or inner membrane. A major lipoprotein, Lpp, is associated with the cell outer membrane at the N-terminus and with peptidoglycan (PG) at the C-terminus. Thus, if Lpp is connected with the OmpA fragment of the cell outer membrane protein, exogenous proteins can be stably expressed onto the cell surface of the cell outer membrane (Francisco, et al., Proc. Natl. Acad. Sci. USA, 89: 2713-2717, 1992). This characteristic has also been used with another lipoprotein, TraT, to express foreign peptides, such as the C3 epitope of the poliovirus, onto a cell surface (Felici, et al., J. Mol. Biol., 222: 301-310, 1991). Furthermore, the peptidoglycan-associated lipoprotein (PAL), although not yet elucidated as regards its precise function, has been adopted to produce recombinant antigens through surface expression (Fuchs, et al., Bio/Technology, 9: 1369-1372, 1991). In this case, the C-terminus of PAL is ligated to the cell wall and the N-terminus to the recombinant antibody so as to express a fusion protein on the cell surface.

Meanwhile, even though secretion proteins that can pass through the cell outer membrane can be used as a surface protein, this has not been developed in Gram-negative bacteria and only a few kinds of secretion proteins can help passage through the cell outer membrane in the presence of specific proteins participating in the secretion mechanism. For example, *Klebsiella* sp. pullulanase as a lipoprotein is completely secreted into a cell culture medium after its N-terminus is substituted with a lipid substance and attached to the cell outer membrane. Kornacker and colleagues expressed β-lactamase onto a cell surface when using the N-terminus fragment of pullulanase, yet the resulting fusion protein of pullulanase-β-lactamase was instantly attached onto the cell surface, then unfortunately separated into the cell culture medium. In addition, this process has also been exploited to produce alkaline phosphatase, a periplasmic space protein, yet the recombinant protein is not stably expressed as at least 14 proteins are required for the secretion (Kornacker, et al., Mol. Microbiol., 4: 1101-1109, 1990).

Moreover, IgA protease, derived from the pathogenic microbe *Neisseria* sp., has a specific secretion system with a fragment signal present at the C-terminus, which makes the protease present at the N-terminus stably attached to the cell outer membrane. Once arriving at the cell outer membrane and protruding on the cell surface, the protease is secreted into the cell culture medium based on its hydrolytic capacity. Klauser and colleagues inconsistently expressed the B subunit of the cholera toxin with a molecular weight of about 12 kDa onto a cell surface using this IgA protease fragment (Klauser, et al., EMBO J., 9: 1991-1999, 1990). However, the secretion of the fused protein was inhibited by the protein folding induced in the cell membrane space during the secretion process.

Besides, in the case of Gram-negative bacteria, the cell suborgans present on the cell surface and applicable for surface expression are composed of flagella, pili, and fimbriae etc. In detail, the B subunit of the cholera toxin and peptides derived from the hepatitis B virus have been consistently produced using flagellin as a subunit composed of flagella and identified as strongly binding with their antibodies (Newton, et al., Science, 244:70-72, 1989). Then, fimbrin, a subunit constituting of threadlike fimbriae on the cell surface, has been utilized to express exogenous peptides, yet only small peptides have been successfully produced (Hedegaard, et al., Gene, 85: 115-124, 1989).

Although the surface proteins of Gram-negative bacteria have already been used to perform surface expression, recently, the surface proteins of Gram-positive bacteria have also been used for surface expression (Samuelson, et al., J. Bacteriol., 177: 1470-1476, 1995). Yet, even in this case, a secretion signal for passing through the cell inner membrane and carrier for surface expression and attaching onto the cell membrane are also needed. In fact, the secretion signal of the lipase derived from *Staphylococcus hyicus* and membrane attachment carrier of protein A derived from *Staphylococcus aureus* have been utilized to produce a malaria blood stage antigen composed of 80 amino acids and albumin attachment protein derived from *Streptococcus* protein G and efficiently express the resulting proteins onto the cell surface.

As described above, since much research has already focused on surface expression with Gram-negative bacteria and Gram-positive bacteria, a number of expression systems have already been developed for the production of valuable proteins and submitted for patent applications, especially in the USA, Europe, and Japan. In detail, 5 patent cases have disclosed the use of the cell outer membrane proteins of Gram negative bacteria (WO 9504069, WO 9324636, WO 9310214, EP 603672, U.S. Pat. No. 5356797), one patent application has reported the use of pili as a cell surface organelle (WO 9410330), and one case using a cell surface lipoprotein (WO 9504079).

As stated above, to express exogenous proteins onto a cell surface using a cell outer membrane protein, the proper cell inner membrane and exogenous protein must be connected on a gene level, induced for biosynthesis, and sustained on the cell outer membrane after passing stably through the cell inner membrane. To accomplish this procedure, a cell inner membrane satisfying the following requirements should be selected, then applied to the carrier for surface expression: above all, the presence of a secretion signal for passing through the cell inner membrane, second, the presence of a targeting signal for stable attachment to the cell outer membrane, third, massive expression onto the cell surface, and fourth, stable expression of the protein, regardless of its size.

However, carriers for surface expression that meet all these requirements have not yet been developed. Currently, only the following disadvantages have been remedied.

Based on such a background, the present inventors investigated the application of a poly-γ-glutamate synthase gene (pgsBCA) derived from a *Bacillus* sp. strain as a novel carrier for surface expression. As a result, a novel expression vent or pgsBCA-containing gene that can efficiently produce exogenous proteins onto microbial surfaces was developed along with a method for successfully expressing exogenous proteins onto microbial surfaces on a large scale.

DISCLOSURE OF INVENTION

The object of the current invention is to provide a method for producing exogenous proteins on a microbial surface.

In detail, in the current invention, a new surface expression carrier that can express foreign proteins onto the surfaces of Gram-negative and Gram-positive microbes on a large scale was selected from the cell outer membrane proteins participating in the synthesis of poly-γ-glutamate from a *Bacillus* sp. strain. Then, utilizing this gene, a surface expression vector that can express exogenous proteins or peptides onto microbial surfaces was constructed and transformed into various kinds of host cell in order to collect cell transformants for surface expression.

To accomplish the objectives of the present invention, a surface expression vector is presented that contains one or more genes encoding a poly-γ-glutamate synthetase complex selected from among pgsb, pgsC, and pgsA.

In detail, the present invention presents a surface expression vector for producing proteins on a microbial surface, in which the pgsB, pgsc, and pgsA genes contain nucleotide sequences that are 80% homologous to those of SEQ ID NO: 1, SEQ ID NO:2, and SEQ ID NO: 3, respectively. In addition, a surface expression vector is also presented for producing proteins on a microbial surface that contain a gene encoding a target protein and transcription termination codon at the C-terminus.

Furthermore, a cell transformant is presented that is transformed using the above expression vector.

Finally, the current invention provides a method for expressing a target protein on a microbial surface of Gram-negative or Gram-positive host cells based on the following steps:

(a) constructing a recombinant expression vector by inserting a gene encoding the target protein into the surface expression vector;

(b) transforming a Gram-negative host cell using the recombinant vector; and (c) cultivating the transformed host cell and expressing the target protein on the surface of the host cell.

BRIEF DESCRIPTION OF DRAWINGS

The above and other objective, features, and advantages of the present invention will be more clearly understood from the following detailed description taken in conjunction with the accompanying drawings, in which;

FIG. 1 depicts the restriction maps of the surface expression vector pGNBCA and recombinant expression vector pGNBCA-HB168, which use Gram-negative bacteria as the host cell in the present invention.

FIG. 2 depicts the surface expression of the hepatitis B virus surface antigen protein in a Gram negative bacterium transformed with the recombinant expression vector pGNBCA-HB168 of the current invention based on performing Western blotting and fluorescence-activated cell sorting assays.

FIG. 3 depicts the restriction maps of the surface expression vector pGNCA and recombinant expression vector pGNCA-HB168 of the present invention.

FIG. 4 depicts the surface expression of the hepatitis B virus surface antigen protein in a Gram-negative bacterium transformed with the surface expression recombinant vectors pGNCA-HB168:A2, pGNCA-HB168:A3, and pGNHB-A: A4 of the present invention based on performing Western blotting and fluorescence-activated cell sorting assays.

FIG. 5 depicts the restriction maps of the surface expression vector pGNA and recombinant expression vector pGNA-HB168 of the current invention.

FIG. 6 depicts the restriction maps of the surface expression vector pGNCA2 and recombinant expression vector pGNHB-A of the current invention.

FIG. 7 depicts the restriction maps of the surface expression vector pGNC and recombinant expression vector pGNC-PreS1 of the current invention.

FIG. 9 depicts the restriction maps of the surface expression vector pHCE1LB:BCA and recombinant expression vector pHCE1LB:BCA-HB168 of the current invention.

FIG. 11 depicts the live vaccine efficacy of a Gram-negative bacterium transformed using the recombinant expression vector pHCE1LB:BCA-HB168 of the current invention.

FIG. 12 depicts the surface expression of the hepatitis B virus surface antigen determinant in a Gram-positive bacterium transformed using the surface expression recombinant vector pHCE1LB:BCA-HB168 of the current invention based on performing Western blotting and fluorescence-activated cell sorting assays.

FIG. 13 depicts the live vaccine efficacy of a Gram-positive bacterium transformed using the recombinant expression vector pHCE1LB:BCA-HB168 of the current invention.

FIG. 14 depicts the restriction maps of the surface expression vector pHCE1LB:A and recombinant expression vectors pHCE1LB:A-TGEN1 and pHCE1LB:A-PEDN of the current invention.

FIG. 15 depicts the surface expression pattern of the TGE virus N protein produced from Gram-negative (*Escherichia coli*) and Gram-positive bacteria transformed using the surface expression recombinant vector pHCE1LB:A-TGEN1 of the current invention based on performing a Western blotting assay.

FIG. 16 depicts the surface expression pattern of the PED virus N protein produced from Gram-negative and Gram-positive bacteria transformed using the expression recombinant vector pHCE1LB:A-PEDN of the current invention based on performing a Western blotting assay.

FIG. 17 depicts the live vaccine efficacy of a Gram-positive bacterium transformed using the recombinant expression vectors pHCE1LB:A-TGEN1 and pHCE1LB:A-PEDN of the current invention.

FIG. 18 depicts the restriction maps of the surface expression vector pHCE1LB:A and recombinant expression vectors pHCE1LB:A-PreS1 and pHCE1LB:A-PreS2 of the current invention.

FIG. 19 depicts the restriction maps of the surface expression vector pHCE1LB:A and recombinant expression vectors pHCE1LB:A-PreS1:PreS2 and pHCE1LB:A-L of the current invention.

FIG. 20 depicts the surface expression pattern of the hepatitis B virus PreS1 and PreS1:PreS2 produced from a Gram-negative bacterium transformed using the expression recombinant vectors pHCE1LB:A-PreS1 and pHCE1LB:A-PreS1: PreS2, respectively, of the current invention and surface expression pattern of the hepatitis B virus L protein produced from a Gram-negative bacterium transformed using the expression recombinant vector pHCE1LB:A-L of the current invention based on performing a Western blotting assay.

FIG. 22 depicts the restriction maps of the recombinant expression vector pGNA-lipase of the current invention and lipase activity expressed onto the cell surface of a Gram-negative bacterium transformed using the recombinant expression vector pGNA-lipase.

FIG. 23 depicts the restriction maps of the recombinant expression vector pGNA-amidase of the current invention and amidase activity expressed onto the cell surface of a Gram-negative bacterium transformed using the recombinant expression vector pGNA-amidase.

BEST MODE FOR CARRYING OUT PRESENT INVENTION

Figure 8:
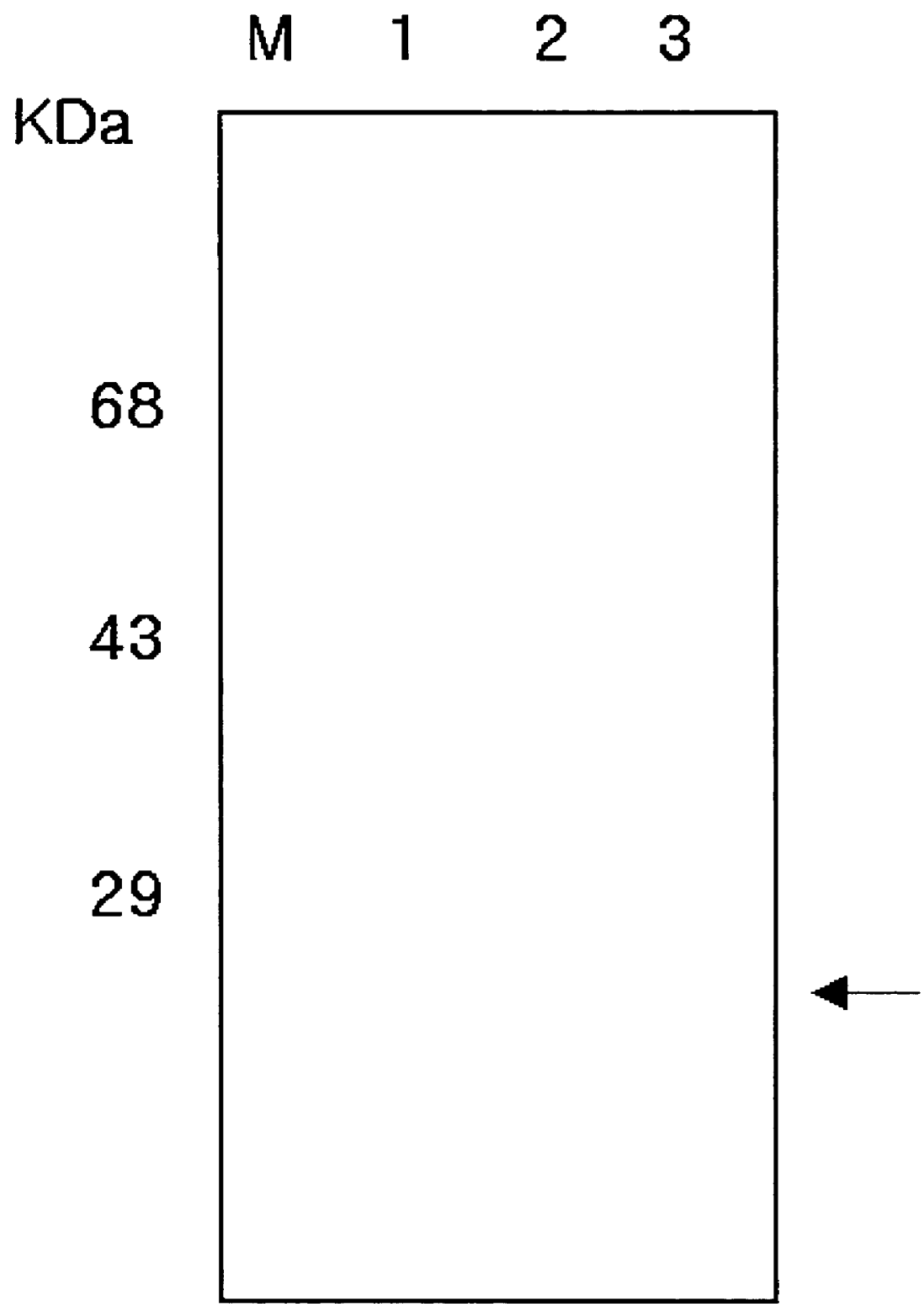
FIG. 8 depicts the surface expression pattern of the hepatitis B virus surface antigen PreS1 protein in a Gram negative bacterium transformed using the surface expression recombinant vector pGNC-PreS1 of the current invention based on performing a Western blotting assay.

Hereinafter, the present invention will be described more clearly.

The protein encoded from the pgsBCA gene is a cell outer protein present in *Bacillus* sp. strains and is polymer substance edible, soluble, anionic, biodegradable participating in the synthesis of poly-γ-glutamate, and produced from *Bacillus subtilis* (IF03336; Natto. Biochem. Biophys. Research Comm., 263, 6-12, 199, *Bacillus licheniformis* (ATCC 9945; Biotech. Bioeng., 4), 430-437, 1998), and *Bacillus anthracis* (J. Bacteriol., 171, 722-730, 1989) etc.

From the Natto strain (*Bacillus subtilis* IFO 3336), a cell membrane protein (pgsBCA) was separated that was composed of a total of 922 amino acids, precisely, 393 amino acids in pgsB, 149 amino acids in pgsC, and 380 amino acid in pgsA. Ashiuchi et al. reported on the cloning of the poly-γ-glutamate synthetase gene derived from the *Bacillus natto* strain, its transformation into *Escherichia coli*, and synthesis (Ashiuchi, et al., Biochem. Biophy. Research Comm, 263: 6-12, 1999).

However, the functions of the pgsBCA protein comprising the poly-γ-glutamate synthetase complex have not yet been elucidated in detail. At least, pgsB is an amide ligase system among the proteins making up the enzyme complex and interacts with the cell membrane or cell wall at a specific amino acid in the N-terminus of pgsB. pgsA has a hydrophilic amino acid sequence specific for the N-terminus and C-terminus that would appear to work as a secretion signal, targeting signal, and attachment signal in association with pgsB for passing through the cell inner membrane.

The present inventors revealed that the cell outer membrane protein participating in the synthesis of poly-γ-glutamate is advantageous as a surface expression carrier and can express exogenous proteins onto a cell surface based on the structure and features of its primary amino acid sequence. Concretely, there are various advantages. First, the cell outer membrane protein participating in the synthesis of poly-γ-glutamate can be expressed on a large scale for the synthesis of poly-γ-glutamate and extracellular secretion; second, the cell outer membrane protein expressed onto the cell surface participating in the synthesis of poly-γ-glutamate can be maintained stably during the rest period of the cell cycle; third, the cell outer membrane protein is structurally protruded on the cell surface, especially in the case of pgsA; fourth, the cell outer membrane protein (pgsBCA) participating in the synthesis of poly-γ-glutamate originates from the cell surface of a Gram-positive bacterium and can be expressed onto the cell surface of either a Gram-positive or Gram negative bacterium.

The present invention provides recombinant expression vectors that are useful for expressing exogenous proteins on a cell surface by exploiting the property of the cell outer membrane participating in the synthesis of poly-γ-glutamate. In detail, the surface expression vectors of the present invention are constructed to contain a secretion signal and targeting signal in the primary sequence of the cell outer membrane protein (pgsBCA) participating in the synthesis of poly-γ-glutamate.

Furthermore, the present invention provides a method for expressing exogenous proteins onto the microbial surface of both Gram-negative and Gram-positive bacteria using the surface expression vector based on exploiting the features of the cell outer membrane protein participating in the synthesis of poly-γ-glutamate. In detail, the method for preparing exogenous proteins in the present invention can omit certain processes, such as cell sonication or protein purification, since the exogenous proteins are expressed onto the cell surface using the cell outer membrane protein participating in the synthesis of poly-γ-glutamate.

Therefore, the present invention provides various uses for exogenous proteins produced through the surface expression method. In detail, the proposed method is effective for producing antigens and antibodies, peptide libraries for screening antigens, attachment proteins or adsorption proteins, and physiologically active substances, etc.

In addition to the cell outer membrane protein participating in the synthesis of poly-γ-glutamate derived from a *Bacillus* sp. strain, all kinds of surface expression vectors containing genes for the synthesis of poly-γ-glutamate can be included within the scope of the present invention.

Moreover, the surface expression vectors using the poly-γ-glutamate synthetase gene in the present invention can be applied to all kinds of microbial strains for surface expression. Preferably, these vectors can be utilized for Gram-negative bacteria, especially *Escherichia coli, Salmonella typhi, Salmonella typhimurium, Vibrio cholera, Mycobacterium bovis*, and *Shigella*, and for Gram-positive bacteria, especially *Bacillus, Lactobacillus, Lactococcus, Staphylococcus, Lysteria, Monocytogenesis*, and *Streptococcus*. All the methods used to manufacture exogenous proteins using these strains can be included within the scope of the present invention.

Depending on the requirements, the poly-γ-glutamate synthetase gene can be manipulated to insert various recognition sites for all or certain restriction enzymes at the N-terminus or C-terminus. Hence, surface expression vectors including these restriction enzyme recognition sites are also within the scope of the present invention.

In detail, the current invention covers all the poly-γ-glutamate synthetase genes derived from *Bacillus* sp. strains. Among these, the pgsA gene is used to insert the restriction enzyme recognition site at the C-terminus and easily clone various kinds of exogenous protein genes, thereby constructing the surface expression vector pGNBCA.

The current invention also presents the recombinant surface expression vector pGNBCA-HB168, which can express an antigenic determinant forming a neutralizing antibody against an S antigen in a fused form onto the cell surface of a Gram negative bacterium. In detail, the cell outer membrane protein complex participating in the synthesis of poly-γ-glutamate is composed of pgsB, pgsC, and pgsA proteins, then the C-terminus of the pgsA protein gene is ligated with the N-terminus of an antigenic determinant forming a neutralizing antibody against the hepatitis B virus S antigen.

The current invention also presents the recombinant surface expression vectors pGNCA-HB168, pGNA-HB168, and pGNHB-A, which can express an antigenic determinant forming a neutralizing antibody against an S antigen in a fused form onto the cell surface of a Gram negative bacterium. In detail, the cell outer membrane protein complex participating in the synthesis of poly-γ-glutamate is composed of either pgsC and pgsA proteins or only pgsA proteins, then the C-terminus of the pgsA protein gene, in the case of the former, or the N-terminus or C-terminus, in the case of the latter, is ligated with the N-terminus of an antigenic determinant forming a neutralizing antibody against the hepatitis B virus S antigen.

The current invention also presents the recombinant surface expression vector pGNC-PreS1, which can express an antigenic determinant forming a neutralizing antibody against an S antigen in a fused form on the cell surface of a Gram negative bacterium. In detail, the cell outer membrane protein complex participating in the synthesis of poly-γ-glutamate is composed of pgsC proteins, then the C-terminus of the pgsC protein gene is ligated with the N-terminus of the PreS1 antigen from among the hepatitis B virus surface antigens.

The current invention also presents the recombinant surface expression vectors pHCE1LB:BCA and pHCE1LB:A, which modify the surface expression vector pGNBCA for a Gram-negative bacterium and can be applied to both Gram-negative and Gram-positive bacteria. In detail, the cell outer membrane protein complex participating in the synthesis of poly-γ-glutamate is composed of either pgsB, pgsc, and pgsA proteins or only pgsA proteins, then the C-terminus of the pgsA protein gene is ligated with the exogenous protein gene.

The current invention also presents the recombinant surface expression vector pHCE1LB:BCA-HB168, which can be applied to both Gram-negative and Gram-positive bacteria and expresses an antigenic determinant forming a neutralizing antibody against an S antigen in a fused form on a cell surface. In detail, the cell outer membrane protein complex participating in the synthesis of poly-γ-glutamate is composed of the pgsB, pgsc, and pgsA proteins, then the C-terminus of the pgsA protein gene is ligated with the N-terminus of an antigenic determinant forming a neutralizing antibody against the hepatitis B virus S antigen.

The current invention also presents the recombinant surface expression vector pHCE1LB:A-TGEN1, which can be applied to both Gram-negative and Gram-positive bacteria and expresses a nucleoprotein N protein onto a cell surface in a fused form. In detail, the cell outer membrane protein complex participating in the synthesis of poly-γ-glutamate is composed of pgsA proteins, then the C-terminus of the pgsA protein gene is ligated with the N-terminus of the partial nucleoprotein gene of the porcine transmissible gastric disease (TGE) virus.

The current invention also presents the recombinant surface expression vector pHCE1LB:A-PEDN, which can be applied to both Gram-negative and Gram-positive bacteria and expresses a nucleoprotein N protein onto a cell surface in a fused form. In detail, the cell outer membrane protein complex participating in the synthesis of poly-γ-glutamate is composed of pgsA proteins, then the C-terminus of the pgsA protein gene is ligated with the N-terminus of the nucleoprotein gene of the porcine diarrhea disease (PED) virus.

The current invention also presents the recombinant surface expression vectors pHCE1LB:A-PreS1, pHCE1LB:A-PreS2, pHCE1LB:A-PreS1:PreS2, and pHCE1LB:A-L, which can be applied to both Gram-negative and Gram-positive bacteria for the surface expression of exPreS1, PreS2, PreS1-PreS2 or total L protein among the hepatitis B virus surface L (PreS1-PreS2-S) proteins, respectively, in a fused form onto a cell surface. In detail, the cell outer membrane protein complex participating in the synthesis of poly-γ-glutamate is composed of pgsA proteins, then the C-terminus of the pgsA protein gene is ligated with the N-terminus of PreS1, PreS2, PreS1-PreS2, or the total L protein, respectively.

The current invention also presents the recombinant surface expression vector pHCE1LB:A-TNF-α, which can be applied to both Gram-negative and Gram-positive bacteria and expresses the TNF-α protein onto a cell surface in a fused form. In detail, the cell outer membrane protein participating in the synthesis of poly-γ-glutamate is composed of pgsA proteins, then the C-terminus pgsA protein gene is ligated with the N-terminus of the tumor necrosis factor α, a cytokine.

The current invention also presents the recombinant surface expression vectors pGNA-lipase and pGNA-amydase, which can be applied to Gram-negative bacteria and express industrial enzymes, such as lipase and amydase, onto a cell surface in a fused form. In detail, the cell outer membrane protein complex participating in the synthesis of poly-γ-glutamate is composed of pgsA proteins, then the C-terminus of the pgsA protein gene is ligated with the N-terminus of a lipase or amydase among enzymes for industrial use.

EXAMPLES

Practical and presently preferred embodiments of the current invention are illustrated in the following examples.

However, it is appreciated that those skilled in the art, on consideration of this disclosure, may make modifications and improvements within the spirit and scope of the present invention.

Example 1

Construction of Surface Expression Vector pGNBCA

To prepare the surface expression vector of the current invention, which uses the cell outer membrane protein gene pgsBCA participating in the synthesis of poly-gamma-glutamate derived from a *Bacillus* sp. strain and a Gram-negative bacterium as the host cell, the total chromosomal DNA of *Bacillus subtilis* var. chungkookjang (accession number: KCTC 0697 BP) was purified.

The gene pgsBCA is composed of pgaB as a DNA fragment containing the nucleotide sequence of SEQ ID NO: 1, pgac as a DNA fragment containing the nucleotide sequence of SEQ ID NO: 2, and pgaA as a DNA fragment containing the nucleotide sequence of SEQ ID NO: 3 and has the above consecutive nucleotide sequences.

To obtain the genes encoding the N-terminus and C-terminus of the cell inner membrane participating in the biosynthesis of poly-γ-glutamate, the total chromosome was adopted as the template and oligonucleotides with the nucleotide sequence of SEQ ID NO: 4 (5-gaa cca tgg gct ggt tac tcc tta tag cct g-3) at the N-terminus and nucleotide sequence of SEQ ID NO: 5 (5-ctc gga tcc ttt aga ttt tag ttt gtc act-3) at the C-terminus used as the primers. Then, a polymerase chain reaction (PCR) was performed using the template and primers.

The oligonucleotide primer of SEQ ID NO: 4 corresponding to the N-terminus was also constructed to contain the restriction enzyme NcoI recognition site present in the expression vector pHCE19T(II), while the oligonucleotide primer of SEQ ID NO: 5 corresponding to the C-terminus was constructed to contain the restriction enzyme BamHI recognition site present in the expression vector pHCE19T(II). At this point, the amplified gene fragment was measured as having a size of 2.8 kb ranging from the N-terminal region of the cell outer membrane protein gene pgsB to the C-terminal region of pgsA. The gene fragment amplified through the PCR was digested with the restriction enzymes NcoI and BamHI and inserted into the constitutively high expression vector pHCE19T(II) digested with NcoI and BamHI. As a result, the new expression vector containing the cell inner membrane protein gene that participates in the synthesis of poly-γ-glutamate did not include a translation termination codon, contained a new additional restriction enzyme recognition site, was about 6.5 kb in size, had the nucleotide sequence of SEQ ID NO: 6, and was named expression vector pGNBCA (See FIG. 1).

The surface expression vector was transformed into *Escherichia coli* and the resulting cell transformant deposited with the International Deposit Organization and Korean Collection for Type Cultures (KCTC: 52 Eoeun-dong, Yusong-gu, Daejon) at the Korean Research Institute of Bioscience and Biotechnology (KRIBB) on Jul. 26, 2001 (accession number: KCTC 10025 BP).

Example 2

Construction of Surface Expression Vector pGNBCA-HB168

The recombinant expression vector pGNBCA-HB168, which can express an antigenic determinant forming a neutralizing antibody against the hepatitis B virus S antigen was constructed using the cell outer membrane protein gene pgsBCA participating in the synthesis of poly-γ-glutamate derived from a *Bacillus* sp. strain and a Gram-negative bacterium as the host cell.

To insert the hepatitis B virus S antigen gene into the surface expression vector pGNBCA using a Gram-negative bacterium as the host cell, the hepatitis B virus gene, about 1.4 kb in size, contained in the general cloning vector pUC8 was adopted as the template and oligonucleotides with the nucleotide sequence of SEQ ID NO: 7 and nucleotide sequence of SEQ ID NO: 8 utilized as the primers. Then, a polymerase chain reaction (PCR) was performed using the template and primers so as to amplify the S antigen gene. As a result, an amplified gene fragment 168 bp in size was obtained.

At this point, the primers with the nucleotide sequence of SEQ ID NO: 7 and nucleotide sequence of SEQ ID NO: 8 were also constructed to contain the restriction enzyme BamHI and HindIII recognition sites. Then, the amplified S antigen gene of the hepatitis B virus was digested with the restriction enzymes BamHI and HindIII and ligated to the already prepared C-terminal region of the cell outer membrane protein gene participating in the synthesis of poly-γ-glutamate by adjusting the translation codons. The resulting recombinant expression vector pGNBCA-HB168 is illustrated in FIG. 1.

Example 3

Surface Expression of Antigenic Determinant Forming Neutralizing Antibodies Against Hepatitis B Virus S Antigen Using Recombinant Expression Vector pGNBCA-HB168

The surface expression of an antigenic determinant forming neutralizing antibodies against the hepatitis B virus S antigen was examined using the recombinant expression vector pGNBCA-HB168.

The expression vector constructed in Example 2 was transformed into *E. coli* and cultivated in a 500 ml flask containing 50 ml of an LB medium (yeast extract 5 g/L, trypton 10 g/L, sodium chloride 5 g/L, pH 7.0) and 100 mg/L of antibiotic ampicillin to induce surface expression.

The bacterial expression of the antigenic determinant forming neutralizing antibodies against the S antigen fused with the C-terminal gene participating in the synthesis of poly-γ-glutamate was identified by performing SDS-polyacrylamide gel electrophoresis and Western immunoblotting with antibodies against the S antigen. Essentially, the proteins obtained at the same cell concentration were denatured so that experimental samples could be prepared and then analyzed through SDS-polyacrylamide gel electrophoresis so that the fractionated proteins were transferred onto a PVDF membrane. The resulting PVDF membrane was then stirred in a blocking buffer (10 ml Tris HCl, 5% skim milk, pH 8.0) for one hour, blocked, and then reacted for 12 hours with a goat-derived polyclonal primary antibody against the S antigen diluted 1,000 times with the blocking buffer. After completing the reaction, the resulting membrane was washed with the same buffer solution and reacted for 4 hours with a secondary antibody conjugated with biotins and diluted 1,000 times with the blocking buffer. The reacted membrane was then washed again with the buffer and immersed in an avidin-biotin reagent for one hour and washed. The submersed membrane was colored by adding substrates and H202 and DAB reagents as dyes, which identified a specific binding with the antibodies against the S antigen and above fusion proteins (See FIG. 2, A). In FIG. 2, lane 1 is the untransformed host cell JM109, while lane 2 is the cell transformant pGNBCA-HB168/JM109. As illustrated, a fusion protein band of about 48 kDa was produced from the expression vector pGNBCA-HB168.

In addition, to directly confirm the expression of an antigenic determinant forming neutralizing antibodies against the hepatitis B virus S antigen situated on the *E. coli* surface, the *E. Coli* transformant inducing the surface expression was sonicated and separated into the soluble fraction, cell inner membrane fraction, and cell outer membrane fraction based on outer membrane fractionation, then analyzed by accomplishing SDS-polyacrylamide gel electrophoresis and Western immunoblotting of the antibodies against the S antigen. Essentially, the *E. coli* transformant used to induce the expression of the fusion protein on the cell surface, as described above, and untransformed *E. coli* were harvested, adjusted to the same concentration, and washed several times using a buffer solution (10 mM HEPES, pH 7.4). Thereafter, the resultant was floated on a buffer containing 10 g/ml lysozyme, 1 mM PMSF, and 1 mM EDTA, reacted at 4° C. for 10 minutes, DNase (0.5 mg/ml) and RNase (0.5 mg/ml) added, the mixture broken with a sonicator, and the intact *E. coli* and cellular debris separated at 4° C. for 20 minutes using 10,000×g of centrifugation. The separated cellular debris of *E. coli* was then centrifuged at 4° C. for 20 minutes at 15,000×g and the fractions containing proteins of periplasm and cytoplasm collected. The resulting cell pellet was immersed in a PBS buffer (pH 7.4) containing 1% Sarcosyl (N-lauryl sarcosinate, sodium salt) and centrifuged at 4° C. for 2 hours at 15,000×g and separated.

At this point, the supernatant was fractionated into the *E. coli* inner membrane and cell pellet of the *E. coli* outer membrane protein, then analyzed based on performing SDS-polyacrylamide gel electrophoresis and Western blotting using antibodies against the S antigen. Among the above *E. coli* fractions, an antigenic determinant forming a neutralizing antibody against the S antigen was identified on the cell outer membrane (See FIG. 2; A: the result of *E. coli* membrane fraction after Western blotting). As illustrated in FIG. 2, lane 1 is the untransformed *E. coli* JM 109 strain, lane 2 is the whole cell of the *E. coli* transformant pGNBCA-HB168/JM109, lane 3 is the soluble fraction of the *E. coli* transformant pGNBCA-HB168/JM109, lane 4 is the cell inner membrane fraction of the *E. coli* transformant pGNBCA-HB168/JM109, and lane 5 is the cell outer membrane fraction of the *E. coli* transformant pGNBCA-HB168/JM109.

An antigenic determinant forming a neutralizing antibody against S antigen was verified as having been expressed onto the *E. coli* cell surface from the C-terminus of the poly-γ-glutamate synthetase protein by performing fluorescence activating cell sorting (FACS) flow cytometry. For immunofluorescence staining, the *E. coli* used to induce the surface expression was harvested at the same cell concentration and washed several times using a PBS buffer (pH 7.4). The resulting cell pellet was then suspended using 1 ml of a buffer containing 1% bovine serum albumin and reacted with goat-derived polyclonal primary antibodies against the S antigen diluted 1,000 times at 4C for 12 hours. After completing the reaction, the resulting cells were washed again several times, suspended using 1 ml of a buffer containing 1% bovine serum albumin, then reacted at 4C for 3 hours with biotin-associated secondary antibodies against the S antigen diluted to 1,000 times. Also, the completely reacted cells were washed several times using a buffer solution, suspended with 0.1 ml of a buffer containing 1% bovine serum albumin, then bound with the streptoavidin-R-phycoerythrin dyeing reagent diluted to 1,000 times, which is specific for biotins.

Thereafter, the *E. coli* cells were rewashed several times and assayed by performing fluorescence activating cell sorting flow cytometry. As a result, an antigenic determinant protein forming a neutralizing antibody against the S antigen was confirmed as having been expressed onto the cell surface, as distinct from the untransformed *E. coli* (See FIG. 2, B). As illustrated in FIG. 2, the white band depicts the untransformed *E. coli* JM109 strain, while the black band is derived from the *E. coli* transformant pGNBCA-HB168/JM109. Consequently, no antigenic determinant protein forming a neutralizing antibody against the S antigen was expressed from the untransformed *E. coli* strain, yet obviously determined from the *E. coli* transformant transformed with the surface expression vector of the current invention.

Example 4

Construction of Recombinant Surface Expression Vector pGNCA-HB101 and Surface Expression of Antigenic Determinant Forming Neutralizing Antibody Against Hepatitis B Virus S Antigen (1) A recombinant expression vector that can express an antigenic determinant forming a neutralizing antibody against the hepatitis B virus S antigen was constructed using the cell outer membrane protein gene pgsBCA participating in the synthesis of poly-γ-glutamate derived from a *Bacillus* sp. strain and a Gram-negative bacterium as the host cell.

The gene pgsCA has a consecutive nucleotide sequence containing the pgsC DNA of SEQ ID NO: 2 and pgaA DNA of SEQ ID NO: 3.

To obtain the N-terminal and C-terminal genes encoding the pgsc and pgsA proteins from the cell outer membrane protein gene participating in the synthesis of poly-γ-glutamate, the total chromosome was utilized as the template and oligonucleotides containing the nucleotide sequences of SEQ ID NO: 9 at the N-terminus and SEQ ID NO: 5 at the C-terminus used as the primers for performing a polymerase chain reaction.

The primer corresponding to the N-terminus and containing the sequence of SEQ ID. NO: 9 was also constructed to include the restriction enzyme NdeI recognition site. At this point, the amplified gene region included about 1.6 kb from the N-terminal region of the outer membrane protein gene pgsC participating in the synthesis of poly-γ-glutamate to the C-terminal region of pgsA.

The genes amplified through the polymerase chain reaction were digested with the restriction enzymes NdeI and BamHI and inserted into the constitutively high expression vector pHCE19T(II) already digested with BamHI and NdeI, thereby creating a new expression vector, about 5.3 kb in size, with new restriction enzyme recognition sites, and no termination codon at the end of the cell outer membrane protein gene, called expression vector pGNCA (See FIG. 3).

(2) The recombinant expression vector pGNCA-HB168 that can express an antigenic determinant forming a neutralizing antibody against the hepatitis B virus S antigen was constructed through the same procedure as described above in Example 2. In detail, the recombinant expression vector was prepared by exploiting the cell outer membrane protein genes pgsc and pgsA from the pgsBCA gene participating in the synthesis of poly-γ-glutamate and a Gram-negative bacterium as the host cell.

The recombinant expression vector pGNCA-HB168 constructed above is depicted in FIG. 3.

(3) The expression of an antigenic determinant forming a neutralizing antibody against the hepatitis B virus S antigen using the surface expression vector pGNCA-HB168 was examined as follows:

The surface expression vector was transformed into a *E. coli* host cell and expression induced using the same procedure as described above in Example 3. Then, an antigenic determinant forming a neutralizing antibody against the S antigen fused with the cell outer membrane protein pgsCA was identified as having been expressed in the *E. coli* transformant based on performing SDS-polyacrylamide gel electrophoresis and Western blotting using antibodies against the S antigen (See FIG. 4).

As illustrated in FIG. 4, lane 1 is the untransformed host cell JM109, while lane 2 is the cell transformant pGNCA-HB168/JM109. As a result, the fused protein expressed from the recombinant expression vector pGNCA-HB168 was identified as a band of about 48 kDa.

Example 5

Construction of Recombinant Surface Expression Vector pGNA-HB168 and Surface Expression of Antigenic Determinant Forming Neutralizing Antibody Against Hepatitis B Virus S Antigen (1) A recombinant expression vector that can express an antigenic determinant forming a neutralizing antibody against the hepatitis B virus S antigen was constructed using the cell outer membrane protein gene pgsA from the pgsBCA gene participating in the synthesis of poly-γ-glutamate derived from a *Bacillus* sp. strain and a Gram-negative bacterium as the host cell.

The gene pgsA contains the nucleotide sequence of SEQ ID NO: 3.

To obtain the N-terminal and C-terminal genes encoding the pgsA protein from the cell outer membrane protein gene participating in the synthesis of poly-γ-glutamate, the total chromosome was utilized as the template and oligonucleotides containing the nucleotide sequences of SEQ ID NO: 10 at the N-terminus and SEQ ID NO: 5 at the C-terminus used as the primers for performing a polymerase chain reaction.

The primer corresponding to the N-terminus and containing the sequence of SEQ ID. NO: 10 was also constructed to include the restriction enzyme NdeI recognition site. At this point, the amplified gene region was about 1.1 kb from the N-terminal region of the outer membrane protein gene pgsA participating in the synthesis of poly-γ-glutamate to the C-terminal region of pgsA.

The genes amplified through the polymerase chain reaction were digested with the restriction enzymes NdeI and BamHI and inserted into the constitutively high expression vector pHCE19T(II) already digested with BamHI and NdeI, thereby creating a new expression vector, about 4.8 kb in size, with new restriction enzyme recognition sites, and no termination codon at the end of the cell outer membrane protein gene, called expression vector pGNCA (See FIG. 5).

(2) The recombinant expression vector pGNCA-HB168 that can express an antigenic determinant forming a neutralizing antibody against the hepatitis B virus S antigen was constructed through the same procedure described above in Example 2. In detail, the recombinant expression vector was prepared by exploiting the cell outer membrane protein gene pgsA from the pgsBCA gene participating in the synthesis of poly-γ-glutamate and a Gram-negative bacterium as the host cell.

The recombinant expression vector pGNA-HB168 constructed above is depicted in FIG. 5.

(3) The expression of an antigenic determinant forming a neutralizing antibody against the hepatitis B virus S antigen using the surface expression vector pGNA-HB168 was examined as follows:

The surface expression vector was transformed into the *E. coli* host cell and expression induced through the same procedure as described above in Example 3. Then, an antigenic determinant forming a neutralizing antibody against the S antigen fused with the cell outer membrane protein pgsCA was identified as having been expressed in the *E. coli* transformant by performing SDS-polyacrylamide gel electrophoresis and Western blotting using antibodies against the S antigen (See FIG. 5).

As illustrated in FIG. 5, lane 1 is the untransformed host cell JM109, while lane 2 is the cell transformant pGNA-HB168/JM109. As a result, the fused protein expressed from the recombinant expression vector pGNA-HB168 was identified as a band of about 48 kDa.

Furthermore, the expression of an antigenic determinant forming a neutralizing antibody against S antigen onto the *E. coli* cell surface from the cell outer membrane protein pgsA was also verified based on performing fluorescence activating cell sorting (FACS) flow cytometry. For this purpose, the same procedure as described above in Example 3 was used, and an antigenic determinant forming a neutralizing antibody against the S antigen was detected on the cell surface, as distinct from the results for the untransformed *E. coli*(See FIG. 4). As illustrated in FIG. 4, the white band is the untransformed *E. coli* JM109, while the black band is derived from the *E. coli* transformant pGNA-HB168/JM109. As a result, the untransformed *E. coli* did not exhibit the expression of an antigenic determinant forming a neutralizing antibody against the S antigen, whereas the *E. coli* transformant transformed with the surface expression vector containing only the pgsA gene clearly revealed the expression of an antigenic determinant forming a neutralizing antibody against the S antigen onto the cell surface.

Example 6

Construction of Recombinant Surface Expression Vector pGNHB-A and Surface Expression of Antigenic Determinant Forming Neutralizing Antibody Against Hepatitis B Virus S Antigen (1) A recombinant expression vector that can express an antigenic determinant forming a neutralizing antibody against the hepatitis B virus S antigen was constructed using the N-terminal pgsA gene from the cell outer membrane protein gene pgsBCA participating in the synthesis of poly-γ-glutamate derived from a *Bacillus* sp. strain and a Gram-negative bacterium as the host cell.

The gene pgsA contains the nucleotide sequence of SEQ ID NO: 3.

To obtain the N-terminal and C-terminal genes encoding the pgsA protein from the cell outer membrane protein gene participating in the synthesis of poly-γ-glutamate, the total chromosome was utilized as the template and oligonucleotides containing the nucleotide sequences of SEQ ID NO: 11 at the N-terminus and SEQ ID NO: 12 at the C-terminus used as the primers for performing a polymerase chain reaction.

The primer corresponding to the N-terminus and containing the sequence of SEQ ID. NO: 11 was also constructed to include the restriction enzyme BamHI recognition site. At this point, the amplified gene region was about 1.1 kb from the N-terminal region of the outer membrane protein gene pgsA participating in the synthesis of poly-γ-glutamate to the C-terminal region of pgsA. The genes amplified through the polymerase chain reaction were digested with the restriction enzymes BamHI and HindIII and inserted into the constitutively high expression vector pHCE19T(II) already digested with BamHI and HindIII, thereby creating a new expression vector called pGNA2, about 4.8 kb in size, with new restriction enzyme recognition sites at the front of the pgsA gene, and no termination codon at the end of the cell outer membrane protein gene participating in the synthesis of poly-γ-glutamate (See FIG. 6).

(2) The recombinant expression vector pGNHB-A that can express an antigenic determinant forming a neutralizing antibody against the hepatitis B virus S antigen was also constructed. In detail, the recombinant expression vector was prepared by exploiting the N-terminal sequence of the cell outer membrane protein gene pgsA from the protein gene pgsBCA participating in the synthesis of poly-γ-glutamate and a Gram-negative bacterium as the host cell.

To insert the hepatitis B virus S antigen gene into the surface expression vector pGNA2, while exploiting a Gram-negative bacterium as the host cell, about 1.4 kb of the hepatitis virus gene cloned into the general cloning vector pUC18 was adopted as the template and oligonucleotides with the nucleotide sequences of SEQ ID NO: 13 and SEQ ID NO: 14 utilized as the primers for amplifying the S antigen gene through a polymerase chain reaction. At this moment point, the amplified gene region was 1.6 bp in size.

The primers with nucleotide sequences of SEQ ID NO: 13 and SEQ ID NO: 14 were also constructed to contain the restriction enzyme NdeI and BamHI recognition sites present in the surface expression vector pGNA2. The amplified genes of the hepatitis B virus S antigen were digested with the restriction enzymes NdeI and BamHI and ligated to the N-terminal region of the pgsA gene from among the cell outer membrane genes participating in the synthesis of poly-γ-glutamate in the surface expression vector pGNA2 already prepared by adjusting the translation codons. The recombinant expression vector pGNHB-A constructed above is depicted in FIG. 6.

(3) The expression of an antigenic determinant forming a neutralizing antibody against the hepatitis B virus S antigen using the surface expression vector pGNHB-A was examined as follows:

The surface expression vector was transformed into the *E. coli* host cell and expression induced using the same procedure described above in Example 3. Then, the identification of an antigenic determinant forming a neutralizing antibody against the S antigen fused with the cell outer membrane protein pgsCA expressed in the *E. coli* transformant was performed based on SDS-polyacrylamide gel electrophoresis and Western blotting using antibodies against the S antigen (See FIG. 5).

As illustrated in FIG. 5, lane 1 is the untransformed host cell JM109, while lane 2 is the cell transformant pGNHB-A/

JM109. As a result, the fused protein expressed from the recombinant expression vector pGNHB-A was identified as a band of about 48 kDa.

Example 7

Construction of Recombinant Surface Expression Vector pGNC-PreS1 and Surface Expression of Antigenic Determinant Forming Neutralizing Antibody Against Hepatitis B Virus PreS1 Antigen (1) A recombinant expression vector that can express an antigenic determinant forming a neutralizing antibody against the hepatitis B virus S antigen was constructed using the C-terminal pgsc gene from the cell outer membrane protein gene pgsBCA participating in the synthesis of poly-γ-glutamate derived from a *Bacillus* sp. strain and a Gram-negative bacterium as the host cell.

The gene pgsC contains the nucleotide sequence of SEQ ID NO: 2.

To obtain the N-terminal and C-terminal genes encoding the pgsA protein from among cell outer membrane proteins participating in the synthesis of poly-γ-glutamate, the total chromosome was utilized as the template and oligonucleotides containing the nucleotide sequences of SEQ ID NO: 15 at the N-terminus and SEQ ID NO: 16 at the C-terminus used as the primers for performing a polymerase chain reaction.

The primer corresponding to the N-terminus and containing the sequence of SEQ ID. NO: 15 was also constructed to include the restriction enzyme NdeI recognition site present in the surface expression vector pHCE 19T(II), while the primer containing the sequence of SEQ ID. NO: 16 was constructed to include the restriction enzyme BamHI recognition site present in the surface expression vector pHCE 19T(II). At this point, the amplified gene region was about 0.45 kb in size from the N-terminal region of the outer membrane protein gene pgsC participating in the synthesis of poly-γ-glutamate to the C-terminal region of pgsC. The genes amplified through the polymerase chain reaction were digested with the restriction enzymes BamHI and NdeI and inserted into the constitutively high expression vector pHCE19T(II) already digested with BamHI and NdeI, thereby creating a new expression vector called pGNC, about 4.1 kb in size, with new restriction enzyme recognition sites, and no termination codon at the end of the cell outer membrane protein gene participating in the synthesis of poly-γ-glutamate (See FIG. 7).

(2) The recombinant expression vector pGNC-PreS1 that can express an antigenic determinant forming a neutralizing antibody against the hepatitis B virus PreS1 surface antigen was also constructed. In detail, the recombinant expression vector was prepared by exploiting the N-terminal sequence of the cell outer membrane protein gene pgsc from the protein gene pgsBCA participating in the synthesis of poly-γ-glutamate and using a Gram-negative bacterium as the host cell.

To insert the hepatitis B virus PreS1 antigen gene into the surface expression vector pGNC, while exploiting a Gram-negative bacterium as the host cell, about 1.5 kb of the hepatitis virus gene cloned into the general cloning vector pUC18 was adopted as the template and oligonucleotides with the nucleotide sequences of SEQ ID NO: 17 and SEQ ID NO: 18 utilized as the primers for amplifying the S antigen gene through a polymerase chain reaction. At this point, the amplified gene region became 356 bp in size.

The primers with the nucleotide sequences of SEQ ID NO: 17 and SEQ ID NO: 18 were also constructed to contain the restriction enzyme HindIII and BamHI recognition sites present in the surface expression vector pGNC. The amplified genes of the hepatitis B virus PreS1 antigen were digested with the restriction enzymes HindIII and BamHI and ligated to the N-terminal region of the pgsc gene from the cell outer membrane gene participating in the synthesis of poly-γ-glutamate in the surface expression vector pGNC already prepared by adjusting the translation codons. The recombinant expression vector pGNC-PreS1 constructed above is depicted in FIG. 7.

(3) The expression of an antigenic determinant forming a neutralizing antibody against the hepatitis B virus S antigen using the surface expression vector pGNC-PreS1 was examined as follows:

The surface expression vector was transformed into the *E. coli* host cell and expression induced using the same procedure described above in Example 3. Then, the identification of an antigenic determinant forming a neutralizing antibody against the PreS1 antigen fused with the cell outer membrane protein pgsc expressed in the *E. coli* transformant was performed based on SDS-polyacrylamide gel electrophoresis and Western blotting using antibodies against the PreS1 antigen (See FIG. 8).

As illustrated in FIG. 8, lane 1 is the untransformed host cell JM109, while lanes 2 and 3 cell and the transformant pGNC-PreS1/JM109. As a result, the fused protein expressed from the recombinant expression vector pGNC-PreS1 was identified as a band of about 27 kDa.

Example 8

Construction of Recombinant Surface Expression Vectors pHCE1LB:BCA and pHCE1LB:BCA-HB168, and Surface Expression of Antigenic Determinant Forming Neutralizing Antibody Against Hepatitis B Virus S Antigen (1) The recombinant expression vector pHCE1LB:BCA that can express an antigenic determinant forming a neutralizing antibody against the hepatitis B virus S antigen onto a cell surface was constructed using the C-terminal pgsC gene from the cell outer membrane protein gene pgsBCA participating in the synthesis of poly-γ-glutamate derived from a *Bacillus* sp. strain and a Gram-negative bacterium as the host cell.

The plasmid pHCE1LB was adopted as the cloning vector as it can replicate and be selected in both Gram-negative and Gram-positive bacteria. The expression vector pHCE1LB was comprised of a constitutively high expressing HCE promoter, plus the cloning site contained various restriction enzyme recognition sites, origins replicable in Gram-negative bacteria, and antibiotic-resistant markers of ampicillin. In addition, the expression vector pHCE1LB was composed of origins replicable in Gram-positive bacteria derived from *Lactobacillus* sp. and antibiotic-resistant markers of chloroamphenicol.

To obtain the N-terminal and C-terminal genes encoding the pgsBCA protein from among the cell outer membrane proteins participating in the synthesis of poly-γ-glutamate, the total chromosome was utilized as the template and oligonucleotides containing the nucleotide sequences of SEQ ID NO: 4 at the N-terminus and SEQ ID NO: 5 at the C-terminus used as the primers for performing a polymerase chain reaction. At this point, the amplified gene region was about 2.8 kb in size from the N-terminal region of the outer membrane protein gene pgsB participating in the synthesis of poly-gamma-glutamate to the C-terminal region of pgsA. The genes amplified through the polymerase chain reaction were digested with the restriction enzymes NcoI and BamHI and inserted into the expression vector pHCE1LB already digested with BamHI and NcoI, thereby creating a new expression vector called pHCE1LB:BCA, about 8 kb in size, with new restriction enzyme recognition sites, no termination codon at the end of the cell outer membrane protein gene participating in the synthesis of poly-γ-glutamate, and utilizing both Gram-negative and Gram-positive bacteria as a host cell (See FIG. 9).

(2) The recombinant expression vector pHCE1LB:BCA-HB168 that can express an antigenic determinant forming a neutralizing antibody against the hepatitis B virus S surface antigen was also constructed. In detail, the recombinant expression vector was prepared using the same procedure described above by exploiting the cell outer membrane protein gene pgsBCA participating in the synthesis of poly-γ-glutamate and using a Gram-negative bacterium as the host cell.

The recombinant expression vector pHCE1LB:BCA-HB168 constructed above is illustrated in FIG. 9.

Figure 10:
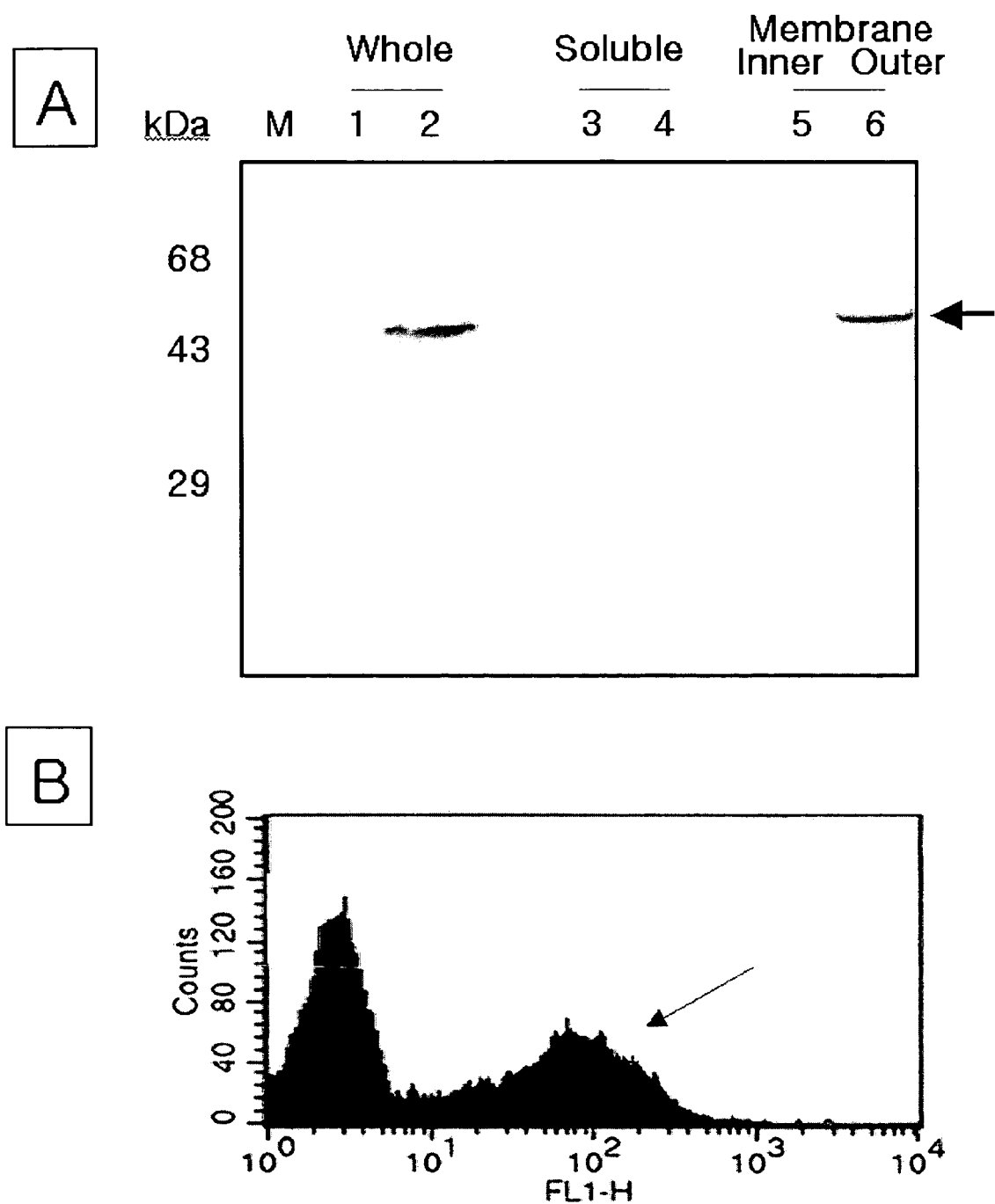
FIG. 10 depicts the surface expression pattern of the hepatitis B virus surface antigen determinant in a Gram-negative bacterium transformed using the surface expression recombinant vector pHCE1LB:BCA-HB168 of the current invention based on performing Western blotting and fluorescence-activated cell sorting assays.

(3) The expression of an antigenic determinant forming a neutralizing antibody against the hepatitis B virus S antigen using the surface expression vector pHCE1LB:BCA-HB168 and *Salmonella typhi* Ty21a as the Gram negative host was investigated as follows:

The surface expression vector was transformed into the *Salmonella typhi* Ty21a host cell and expression induced using the same procedure described above in Example 3. Then, the identification of an antigenic determinant expressed onto the cell surface of *Salmonella typhi* Ty21a was conducted based on the outer membrane fractionation method by separating the soluble fraction, inner membrane fraction, and outer membrane fraction and performing SDS-polyacrylamide gel electrophoresis and Western immunoblotting using antibodies against the S antigen. As a result, the production of an antigenic determinant forming a neutralizing antibody against the S antigen fused with pgsA, corresponding to a 48 kDa band, was confirmed to be situated in the outer membrane fraction among the *Salmonella typhi* Ty21a fractions (See FIG. 10). As illustrated in FIG. 10, lane 1 is the untransformed host cell, lane 2 is the whole cell of the cell transformant, and lanes 3, 4, and 5 are the soluble fraction, inner membrane fraction, and outer membrane fraction, respectively, of the cell transformant.

In addition, the surface expression of an antigenic determinant forming a neutralizing antibody against the S antigen was verified by performing fluorescence activating cell sorting (FACS) flow cytometry. For this purpose, the same procedure was used as described above in Example 3, which revealed an antigenic determinant protein on the cell surface, as distinct from the result for the untransformed *Salmonella typhi* Ty21a (See FIG. 10). As illustrated in FIG. 10, black without an arrow is the untransformed *Salmonella typhi* Ty21a, while black with an arrow is the transformed *Salmonella typhi* Ty21a. As a result, the *E. coli* transformant transformed with the surface expression vector clearly exhibited the expression of an antigenic determinant forming a neutralizing antibody against the S antigen onto the cell surface.

Example 9

Analysis of Vaccine Efficacy in Mirobes Expressing Antigenic Determinant Forming Neutralizing Antibody Against Hepatitis B Virus S Antigen onto Cell Surface The recombinant vector pHCE1LB:BCA-HB168 constructed for surface expression in Example 8 was transformed into the Gram-negative bacterium, *Salmonella typhi* Ty21a, and expression induced onto the cell surface using the same procedure as described in Example 3. Thereafter, the antigenicity of the antigenic determinant forming a neutralizing antibody against the hepatitis B virus S antigen fused with the cell outer membrane protein participating in the synthesis of poly-γ-glutamate was measured.

Essentially, the recombinant vector pHCE1LB:BCA-HB168 for surface expression was transformed into *Salmonella typhi* Ty21a and the expression of the above antigens examined. Thereafter, some of the *Samonella* strain was administered to the nasal cavity of BALB/c mice, then after several days, (1) the blood serum of the mice was collected and the presence of IgG antibodies against the S antigen examined in the serum, and (2) the organs of the mice were collected, then the presence of IgA antibodies against the S antigen in the suspension solution used to wash the organs was investigated using an enzyme-linked immunosorbent assay (ELISA).

At this point, the harvested cells were washed several times using a PBS buffer (pH 7.4) and adjusted to the same cell concentration, then $2\times10^9$ of *Salmonella typhi* Ty21a on which the antigens had been surface-expressed was administered to the nasal cavity of 4~6 week-old BALB/c mice twice with a 3-day interval in between. After 4 weeks, two further injections were administered with a 3-day interval in between, then, 2 weeks later the blood serum of the mice and solution used to wash the organs were collected and measured for their antibody titers against the antigens based on the ELISA method using the S antigen (See FIG. 11).

As illustrated in FIG. 11, graph A shows the IgG antibody titers against the S antigenic determinant in the blood serum: i.e. the titers of the untransformed *Salmonella*, titers of the *Samonella* transformed with the expression vector pHCE1LB:BCA-HB168, and titers of the *Salmonella* transformed with the expression vector pHCE1LB:HB168. In FIG. 11, graph B shows the IgA antibody titers against the S antigenic determinant in the organs: i.e. the titers of untransformed *Salmonella*, titers of the *Salmonella* transformed with the expression vector pHCE1LB:HB168, and titers of the *Salmonella* transformed with the expression vector pHCE1LB:BCA-HB168.

As demonstrated in FIG. 11, the blood serum and solution used to wash the organs from the BALB/c mice group administered with the *Salmonella typhi* Ty21a transformant transformed with the surface expression vector pHCE1LB:BCA-HB168 exhibited much higher antibody titers for IgG and IgA, as distinct from the results of the other groups.

Accordingly, the microbes of the current invention expressing an antigenic determinant forming a neutralizing antibody against the hepatitis B virus S antigen onto a cell surface were confirmed to work as an effective live vaccine.

Example 10

Surface Expression of Antigenic Determinant Forming Neutralizing Antibody Against Hepatitis B Virus S Antigen onto Gram Positive Bacterium Transformed with Expression Vector pHCE1LB:BCA-HB168

The surface expression of an antigenic determinant forming a neutralizing antibody against the hepatitis B virus S antigen onto the Gram-positive bacterium *Lactobacillus casei* transformed with the recombinant vector pHCE1LB: BCA-HB168 constructed for surface expression, as described in Example 8, was investigated.

The recombinant vector used for the surface expression, as prepared above, was transformed into *Lactobacillus casei* and cultivated in a static state in a 500 ml flask containing 200 ml of an MRS medium, plus 50 mg/L of the antibiotic chloroamphenicol to induce the surface expression.

To locate the antigenic determinant situated on the cell surface of *Lactobacillus casei*, the cell transformants were separated using the cell wall fractionation method into fractions, such as the cell cytoplasm and cell wall etc., and analyzed by performing SDS-polyacrylamide gel electrophoresis and Western blotting using antibodies against the S antigen. Essentially, the *Lactobacillus* transformant induced to express the fused proteins onto the cell surface and untransformed *Lactobacillus* were harvested based on the same cell concentration, washed several times using a TES buffer (10 mM Tris-HCl, pH 8.0, 1 MM EDTA, 25% sucrose), suspended using distilled water containing 5 mg/ml lysozyme, 1 mM PMSF, and 1 mM EDTA, then frozen and dissolved at −60° C. and room temperature, respectively, several times. The resulting cells were disrupted using a sonicator by adding 0.5 mg/ml of DNase and 0.5 mg/ml of RNase. Thereafter, the sonicated cell solution was centrifuged at 4C for 20 minutes at 10,000×g for separation into a whole *Lactobacillus* pellet (whole cell fraction), i.e. not sonicated, and cellular debris (supernatant), then centrifuged again at 4C for one hour at 21,000×g to collect a supernatant containing the cytoplasmic proteins of *Lactobacillus* and a cell pellet. The resulting cell pellet was suspended in a TE buffer (10 mM Tris-HCl, pH 8.0, 1 mM EDTA, pH 7.4) containing 1% SDS to collect the cell wall proteins (cell wall fractions) of *Lactobacillus*.

Each fraction was analyzed to confirm the sites on the cell wall where an antigenic determinant formed a neutralizing antibody against the S antigen by performing SDS-polyacrylamide gel electrophoresis and Western immunoblotting using antibodies against the S antigen (See FIG. 12A). As illustrated in FIG. 12, lanes 1, 3, and 5 are the untransformed *Lactobacillus casei*, lane 2 is the whole cell of *Lactobacillus casei* transformed with the expression vector pHCE1B:BCA-HB168, and lanes 4 and 6 are the soluble fraction and cell wall fraction, respectively, of the transformed cell.

In addition, the surface expression of the antigenic determinant forming a neutralizing antibody against the S antigen from the C-terminus of the poly-gamma-glutamate synthetase protein was verified by performing fluorescence activating cell sorting (FACS) flow cytometry. For this purpose, the same procedure was used as described for Example 3, which revealed an antigenic determinant protein on the cell surface, as distinct from the result for the untransformed *Lactobacillus* (See FIG. 12B). As illustrated in FIG. 12B, the white band is the untransformed *Lactobacillus*, while the black band is derived from the *Lactobacillus* transformed with the expression vector pHCE1LB:BCA-HB168. As a result, the *Lactobacillus* transformant transformed with the surface expression vector clearly exhibited the expression of an antigenic determinant forming a neutralizing antibody against the S antigen onto the cell surface.

Example 11

Analysis of Vaccine Efficacy 2 in Microbes Expressing Antigenic Determinant Forming Neutralizing Antibody Against Hepatitis B Virus S Antigen onto Cell Surface The recombinant vector pHCE1LB:BCA-HB168 constructed for surface expression in Example 8 was transformed into the Gram-positive bacterium *Lactobacillus casei* and expression induced onto the cell surface using the same procedure as described in Example 3. Thereafter, the antigenicity of the antigenic determinant forming a neutralizing antibody against the hepatitis B virus S antigen fused with the cell outer membrane protein participating in the synthesis of poly-γ-glutamate was measured.

Essentially, the recombinant vector pHCE1LB:BCA-HB168 created for surface expression was transformed into *Lactobacillus casei*, harvested to reach the same cell concentration, and washed several times using a PBS buffer (pH 7.4). Then, $5\times10^{10}$ cells of *Lactobacillus* on which the antigens had been surface-expressed were administered to the oral cavity of BALB/c mice 4~6 weeks of age three times a day interval in between, then after 4 weeks 3 more injections were given one day apart. In addition, $1\times10^{10}$ cells of *Lactobacillus* on which the antigens had been surface-expressed were administered to the nasal cavity of BALB/c mice twice with a 3-day interval in between and after 4 weeks 2 further injections with a 3-day interval in between. Two weeks after the oral and nasal administrations, the (1) blood serum of the mice was collected and the IgG antibody titers against the S antigen examined, and (2) the organs of the mice were collected and the IgA antibody titers against the S antigen investigated in the suspension solution used to wash the the organ using an enzyme-linked immunosorbent assay (ELISA)(See FIG. 13).

As illustrated in FIG. 13, graph A shows the IgG antibody titers against the S antigenic determinant for the blood serum: i.e. the titers of the *Lactobacillus* transformed with the expression vector pHCE1LB:BCA-HB168 in the nasal administered group, titers of the *Lactobacillus* transformed with the expression vector pHCE1LB:BCA-HB168 in the oral administered group, titers of the *Lactobacillus* transformed with the expression vector pHCE1LB:HB168 (in which the pgsBCA gene is deleted and from which HB168 can be expressed in the cells) in the oral administered group, and titers of the untransformed *Lactobacillus* in the oral administered group. In FIG. 13, graph B shows the IgA antibody titers against the S antigenic determinant for the organs: i.e. the titers of the untransformed *Lactobacillus*, titers of the *Lactobacillus* transformed with the expression vector pHCE1LB:HB168, titers of the *Lactobacillus* transformed with the expression vector pHCE1LB:BCA-HB168. The experiments were performed using separate groups: nasal administered group and oral administered group.

As demonstrated in FIG. 11, the blood serum and solution used to wash the organs from the BALB/c mice group administered the *Lactobacillus* transformant transformed with the surface expression vector pHCE1LB:BCA-HB168 exhibited much higher antibody titers for IgG and IgA, as distinct from the results for the comparative groups.

Accordingly, the microbes of the current invention expressing an antigenic determinant forming a neutralizing antibody against the hepatitis B virus S antigen onto a cell surface were confirmed to work as an effective live vaccine.

Example 12

Construction of Surface Expression Vector pHCE1LB:A

A recombinant expression vector that can express an antigenic determinant forming a neutralizing antibody against the hepatitis B virus S antigen was constructed using only the cell outer membrane protein gene pgsA from the pgsBCA gene participating in the synthesis of poly-γ-glutamate derived from a *Bacillus* sp. Strain: i.e. the surface expression vector pHCE1LB:A, which can exploit Gram-negative or Gram-positive bacteria as the host cell.

To obtain the N-terminal and C-terminal genes encoding the pgsA protein among the cell outer membrane proteins participating in the synthesis of poly-γ-glutamate, the total chromosome was utilized as the template and oligonucleotides containing the nucleotide sequences of SEQ ID NO: 10 at the N-terminus and SEQ ID NO: 5 at the C-terminus used as the primers for performing a polymerase chain reaction.

At this point, the amplified gene region was about 1.1 kb in size from the N-terminal region of the outer membrane protein gene pgsA participating in the synthesis of poly-γ-glutamate to the C-terminal region. The genes amplified through the polymerase chain reaction were digested with the restriction enzymes NdeI and BamHI and inserted into the expression vector pHCE1LB already digested with BamHI and NdeI, thereby creating a new expression vector, called pGNCA, about 6.3 kb in size, with new restriction enzyme recognition sites, no termination codon at the end of the cell outer membrane protein gene, and the ability to exploit both Gram-negative and Gram-positive bacteria as a host cell (See FIG. 14).

Example 13

Construction of Recombinant Surface Expression Vector pHCE1LB:A-TGEN1 and Surface Expression of TGE N Antigen The recombinant expression vector pHCE1LB:A-TGEN1 that can express a nucleoprotein (N) antigen of the transmissible gastroenteritis virus (TGE) inducing porcine transmissible gastric diseases onto a cell surface was constructed using the pgsA gene from the cell outer membrane protein gene pgsBCA participating in the synthesis of poly-γ-glutamate derived from a *Bacillus* sp. strain and Gram-negative or Gram positive bacteria as the host cell.

To introduce the major antigenic determinant region of the N antigen genes of the TGE virus to the surface expression vector pHCE1LB:A, as prepared in Example 12, using Gram-negative or Gram-positive bacteria as the host cell, about 1.1 kb of the TGE virus gene was cloned into the general cloning vector pUC8 and adopted as the template and oligonucleotides with the nucleotide sequences of SEQ ID NO: 19 and SEQ ID NO: 20 utilized as the primer for performing a polymerase chain reaction (PCR) to amplify the S antigen gene. As a result, an amplified gene fragment 415 bp in size was obtained. At this point, the primers with the nucleotide sequences of SEQ ID NO: 19 and SEQ ID NO: 20 were also constructed to contain the restriction enzyme BamHI and HindIII recognition sites present in the surface expression vector pHCE1LB:A.

Thereafter, the amplified N antigen gene of the TGE virus was digested with the restriction enzymes BamHI and HindIII and ligated to the already prepared C-terminal region of the cell outer membrane protein gene pgsA in the surface expression vector pHCE1LB:A by adjusting the translation codons. The resulting recombinant expression vector pHCE1LB:A-TGEN1 is illustrated in FIG. 1.

The surface expression of the TGE virus N antigen was investigated with *E. coli* and *Lactobacillus* using the recombinant expression vector pHCE1LB:A-TGEN1. For this purpose, the recombinant expression vector was transformed into *E. coli* and *Lactobacillus* and expression induced through the same procedure as described above. The expression of the TGE N antigen fused with the cell outer membrane protein onto the cell surface was then confirmed by performing SDS-polyacrylamide gel electrophoresis and Western immunoblotting using an antibody to the TGE N antigen and pgsA protein, respectively (See FIG. 15).

As illustrated in FIG. 15, in A, lane 1 is the untransformed host cell JM109 and lanes 2 and 3 are the cell transformant pHCE1LB:A-TGEN1/JM109, while in B, lane 1 is the untransformed host cell *Lactobacillus casei*, and lanes 3 and 4 are the *Lactobacillus casei* transformant pHCE1LB:A-TGEN1. As a result, the band corresponding to the fused protein produced from the expression vector pHCE1LB:A-TGEN1 was identified as about 57 kDa in size.

Example 14

Construction of Recombinant Surface Expression Vector pHCE1LB:A-PEDN and Surface Expression of PED N Antigen (1) The recombinant expression vector pHCE1LB:A-PEDN that can express a nucleoprotein (N) antigen of the porcine epidemic diarrhea virus (PED) inducing porcine transmissible gastric diseases onto a cell surface was constructed using the pgsA gene from the cell outer membrane protein gene pgsBCA participating in the synthesis of poly-γ-glutamate derived from a *Bacillus* sp. strain and Gram-negative or Gram-positive bacteria as the host cell.

To introduce the antigenic determinant region of N antigen genes of the PED virus into the surface expression vector pHCE1LB:A, as prepared in Example 12, using Gram-negative or Gram-positive bacteria as the host cell, about 1.3kb of the PED virus gene was cloned into the general cloning vector pUC8 and adopted as the template and oligonucleotides with the nucleotide sequences of SEQ ID NO: 21 and SEQ ID NO: 22 utilized as the primers for performing a polymerase chain reaction (PCR) to amplify the S antigen gene. As a result, an amplified gene fragment 1326 bp in size was obtained. At this point, the primers with the nucleotide sequences of SEQ ID NO: 21 and SEQ ID NO: 22 were also constructed to contain the restriction enzyme BamHI and HindIII recognition sites present in the surface expression vector pHCE1LB:A.

Thereafter, the amplified N antigen gene of the PED virus was digested with the restriction enzymes BamHI and HindIII and ligated to the already prepared C-terminal region of the cell outer membrane protein gene pgsA in the surface expression vector pHCE1LB:A by adjusting the translation codons. The resulting recombinant expression vector pHCE1LB:A-PEDN is illustrated in FIG. 14.

(2). The surface expression of the PED virus N antigen onto *E. coli* and *Lactobacillus* was investigated using the recombinant expression vector pHCE1LB:A-PEDN. For this purpose, the recombinant expression vector was transformed into *E. coli* and *Lactobacillus* and expression induced through the same procedure as described above. Then, the expression of the PED N antigen fused with the cell outer membrane protein pgsA onto the cell surface was confirmed by performing SDS-polyacrylamide gel electrophoresis and Western immunoblotting using an antibody against the PED N antigen and pgsA protein, respectively (See FIG. 16).

As illustrated in FIG. 16, in A, lane 1 is the untransformed host cell JM109, and lanes 2 and 3 are the cell transformant pHCE1LB:A-TGEN1/JM109, while in B, lane 1 is the untransformed host cell *Lactobacillus casei*, lane 2 is the *Lactobacillus casei* transformant pHCE1LB:A, and lane 3 is the *Lactobacillus casei* transformant pHCE1LB:A-PEDN.

As described in the figures, the band corresponding to the fused protein produced from the expression vector pHCE1LB:A-PEDN was identified as about 90 kDa in size.

Example 15

Analysis of Vaccine Efficacy 2 in *Lactobacillus* Expressing N Antigen of TGE Virus and PED Virus onto Cell Surface The recombinant vectors pHCE1LB:A-TGEN1 and pHCE1LB:A-PEDN constructed for surface expression in Examples 13 and 14, respectively, were transformed into the Gram positive bacterium, *Lactobacillus casei* and expression induced onto the cell surface through the same procedure as described in Example 3. Thereafter, the antigenicities of the TGE virus N antigen and PED virus N antigen fused with the cell outer membrane protein pgsA participating in the synthesis of poly-γ-glutamate were measured.

Essentially, the recombinant vectors pHCE1LB:A-TGEN1 and pHCE1LB:A-PEDN created for surface expression were transformed into *Lactobacillus casei*, harvested to reach the same cell concentrations, and washed several times using a PBS buffer (pH 7.4). Then, 5×10 cells of the *Lactobacillus* strain on which the N antigens had been surface-expressed were administered orally and independently to BALB/c mice 4~6 weeks of age three times with a one-day interval in between, then after 1 week injected three times with a one-day interval in between. Four weeks after the first administration, (1) the blood serum of the mice was collected and the production of IgG antibodies against the N antigens examined by performing western blotting with the N antigens (See FIG. 17).

Consequently, as illustrated in FIG. 17, the blood serum from the BALB/c mice group administered the *Lactobacillus* transformant transformed with either the surface expression vector pHCE1LB:A-TGEN1 (A) or pHCE1LB:A-PEDN (B) was found to include antibodies against the N antigens.

Example 16

Construction of Recombinant Expression Vector pHCE1LB:A-PreS1 and Surface Expression of PreS1 Antigen (1) A recombinant expression vector that can express the PreS1 antigen from the hepatitis B virus S antigen onto a cell surface was constructed using only the cell outer membrane protein gene pgsA from the pgsBCA gene participating in the synthesis of poly-γ-glutamate derived from a *Bacillus* sp. strain, i.e. the surface expression vector pHCE1LB:A-PreS1, which can exploit both Gram-negative and Gram-positive bacteria as a host cell.

To introduce the PreS1 antigenic determinant from among the hepatitis B virus surface antigens into the surface expression vector pHCE1LB:A, as prepared in Example 12, using Gram-positive or Gram-negative bacteria as the host cell, about 1.5 kb of the hepatitis B virus gene was cloned into the general cloning vector pUC8 and utilized as the template and oligonucleotides containing the nucleotide sequences of SEQ ID NO: 17 and SEQ ID NO: 18 used as the primers for performing a polymerase chain reaction.

At this point, the amplified HBV S antigen gene was digested with the restriction enzymes BamHI and HindIII and ligated into the expression vector pHCE1LB:A prepared by adjusting the translation codon at the C-terminus of the cell outer membrane protein gene pgsA, thereby creating a new recombinant expression vector, called pHCE1LB:A-PreS1, as illustrated in FIG. 18.

(2) The surface expression of the HBV PreS1 antigen was investigated in *E. coli* using the recombinant expression vector pHCE1LB:A-PreS1. For this purpose, the recombinant expression vector was transformed into *E. coli* and expression induced using the same procedure as described in Example 3. Then, the expression of the PreS1 antigen fused with cell outer membrane protein pgsA onto the cell surface was confirmed by performing SDS-polyacrylamide gel electrophoresis and Western immunoblotting using an antibody against the PreS1 antigen (See FIG. 20 in A).

As illustrated in FIG. 20, in A, lane 1 is the untransformed host cell JM109 and lane 2 is the cell transformant pHCE1LB:A-PreS1/JM109.

As a result, the band corresponding to the fused protein produced from the expression vector pHCE1LB:A-TGEN1 was identified to be about 55 kDa in size.

Example 17

Construction of Recombinant Surface Expression Vector pHCE1LB:A-PreS2

The recombinant expression vector pHCE1LB:A-PreS2 that can express the PreS2 antigen from among the hepatitis B virus surface antigens onto a cell surface was constructed using the pgsA gene from the cell outer membrane protein gene pgsBCA participating in the synthesis of poly-γ-glutamate derived from a *Bacillus* sp. strain and Gram negative or Gram positive bacteria as the host cell.

To introduce the antigenic determinant region of the PreS2 antigen genes of the hepatitis B virus into the surface expression vector pHCE1LB:A, as prepared in Example 12, using Gram negative or Gram positive bacterium as the host cell, about 1.3 kb of the hepatitis B virus gene was cloned into the general cloning vector pUC8 and adopted as the template and oligonucleotides with the nucleotide sequences of SEQ ID NO: 23 and SEQ ID NO: 24 utilized as the primers for performing a PCR to amplify the PreS2 antigen gene. At this point, the amplified gene region was about 165 bp in size. The primers with SEQ ID NO: 23 and SEQ ID NO: 24 were also constructed to include the restriction enzyme BamHI and HindIII recognition sites present in the surface expression vector pHCE1LB:A.

The PreS2 antigen gene of the HBV amplified through the polymerase chain reaction was digested with the restriction enzymes BamHI and HindIII and inserted into the C-terminal region of the cell outer membrane protein gene pgsA in the surface expression vector pHCE1LB:A already digested by adjusting the translation codon, thereby creating the new recombinant expression vector pHCE1LB:A-PreS2, as illustrated in FIG. 18.

Example 18

Construction of Recombinant Expression Vector pHCE1LB:A-PreS1:PreS2 and Surface Expression of PreS1 Antigen (1) A recombinant expression vector that can express a fused form of the PreS1 antigen and PreS2 antigens from among the hepatitis B virus surface antigens onto a cell surface was constructed using only the cell outer membrane protein gene pgsA from the pgsBCA gene participating in the synthesis of poly-γ-glutamate derived from a *Bacillus* sp. Strain: i.e. the surface expression vector pHCE1LB:A-PreS1: PreS2, which can exploit Gram-negative or Gram-positive bacteria as the host cell.

To introduce the PreS1 and PreS2 antigenic determinants from among the hepatitis B virus surface antigens to the surface expression vector pHCE1LB:A, as prepared in Example 12, using Gram-positive or Gram-negative bacteria as the host cell, about 1.5 kb of the hepatitis B virus gene was cloned into the general cloning vector pUC8 and utilized as the template and oligonucleotides containing the nucleotide sequences of SEQ ID NO: 17 and SEQ ID NO: 24 used as the primers for performing a polymerase chain reaction. At this point, the amplified region of the genes was 522 bp in size.

The amplified HBV PreS1:PreS2 antigen genes were digested with the restriction enzymes BamHI and HindIII and ligated into the expression vector pHCE1LB:A prepared by adjusting the translation codon at the C-terminus of the cell outer membrane protein gene pgsA, thereby creating the new recombinant expression vector pHCE1LB:A-PreS1:PreS2, as illustrated in FIG. 19.

(2) The surface expression of the HBV PreS1 and PreS2 antigens was investigated in *E. coli* using the recombinant expression vector pHCE1LB:A-PreS1:PreS2. For this purpose, the recombinant expression vector was transformed into *E. coli* and expression induced using the same procedure as described in Example 3. Then, the expression of the PreS1: preS2 antigen fused with the cell outer membrane protein pgsA onto the cell surface was confirmed by performing SDS-polyacrylamide gel electrophoresis and Western immunoblotting using an antibody to the PreS1 antigen (See FIG. 20 in A). As illustrated in FIG. 20, in A, lane 1 is the untransformed host cell JM109 and lane 3 is the cell transformant pHCE1LB:A-PreS1:PreS2/JM109.

As a result, the band corresponding to the fused protein produced from the expression vector pHCE1LB:A-TGEN1 was identified to be about 60 kDa in size.

Example 19

Construction of Recombinant Surface Expression Vector pHCE1LB:A-L and Surface Expression of L Antigen (1) The recombinant expression vector pHCE1LB:A-L that can express a fused form of the PreS1, PreS2, and S antigens from among the hepatitis B virus surface antigens onto a cell surface was constructed using the pgsA gene from the cell outer membrane protein gene pgsBCA participating in the synthesis of poly-γ-glutamate derived from a *Bacillus* sp. strain and Gram-positive or Gram-negative bacteria as the host cell. The primers with SEQ ID NO: 25 were also constructed to include the restriction enzyme BamHI and HindIII recognition sites present in the surface expression vector pHCE1LB:A.

The amplified L gene of the hepatitis B virus was digested with the restriction enzymes HindIII and BamHI and ligated to the C-terminal region of the pgsA gene from the cell outer membrane gene prepared by adjusting the translation codons. The recombinant expression vector pHCE1LB:A-L is illustrated in FIG. 19.

(3) The surface expression of the L antigen, as a fused antigen composed of the PreS1, PreS2, and S antigens, using the surface expression vector pHCE1LB:A-L was examined in *E. coli*. For this purpose, the surface expression vector was transformed into *E. coli* host cells and expression induced using the same procedure as described in Example 3. Then, the expression of the L antigen fused with the cell outer membrane protein pgsA in the *E. coli* transformant was confirmed by performing SDS-polyacrylamide gel electrophoresis and Western blotting using antibodies to the PreS1 antigen (See FIG. 20, B). As illustrated in FIG. 20, lane 1 is the untransformed host cell JM109 and lanes 2 and 3 are the cell transformant pHCE1LB:A/JM109.

As a result, the fused protein expressed from the recombinant expression vector pHCE1LB:A-L was identified as a band of about 86 kDa.

Example 20

Construction of Recombinant Surface Expression Vector pHCE1LB:A-TNF-α

The recombinant expression vector pHCE1LB:A-TNF-α that can express a fused form of the tumor necrosis factor α (TNF-α), a protein for pharmaceutical and clinical use, onto a cell surface was constructed using the pgsA gene from the cell outer membrane protein gene pgsBCA participating in the synthesis of poly-γ-glutamate derived from a *Bacillus* sp. strain and Gram-positive or Gram-negative bacteria as the host cell.

To introduce the TNF-α gene to the surface expression vector pHCE1LB:A, as constructed in Example 12, using Gram-positive or Gram-negative bacterium as the host cell, about 0.5 kb of the TNF-α gene was cloned into the general cloning vector pUC8 and utilized as the template and oligonucleotides containing the nucleotide sequences of SEQ ID NO: 26 and SEQ ID NO: 27 used as the primers for performing a polymerase chain reaction. At this point, the amplified region of the genes was 482 bp in size. The primers with SEQ ID NO: 26 and SEQ ID NO: 27 were also constructed to include the restriction enzyme BamHI and HindIII recognition sites present in the surface expression vector pHCE1LB: A.

Figure 21:
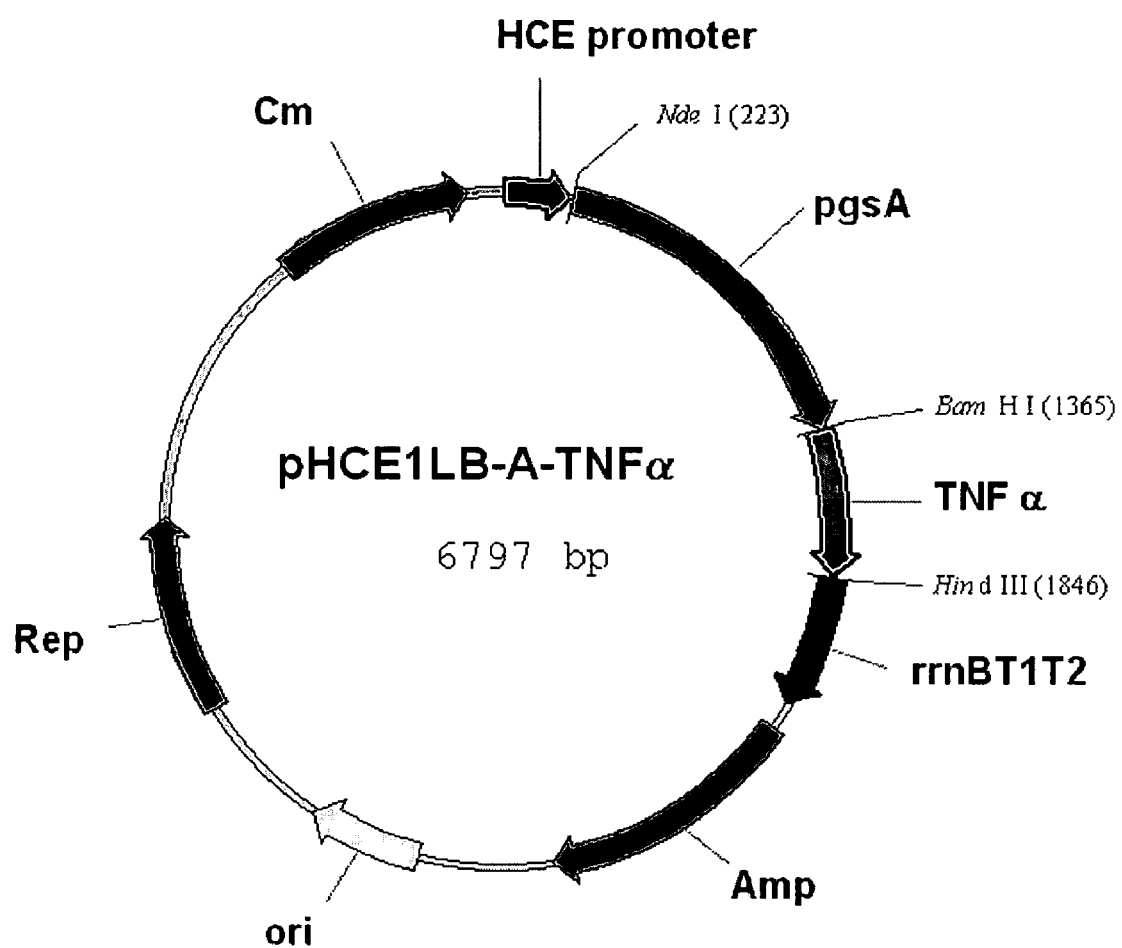
FIG. 21 depicts the restriction maps of the surface expression vector pHCE1LB:A-TNF-α of the current invention.

The amplified L gene of the hepatitis B virus was digested with the restriction enzymes HindIII and BamHI and ligated to the C-terminal region of the cell outer membrane gene participating in the synthesis of poly-γ-glutamate by adjusting the translation codons. The recombinant expression vector pHCE1LB:A-TNF-α constructed above is depicted in FIG. 21.

Example 21

Construction of Recombinant Surface Expression Vector pGNA-lipase and Surface Expression of Lipase The recombinant expression vector pGNA-lipase that can express the lipase enzyme onto a cell surface was constructed using the pgsA gene from the cell outer membrane protein gene pgsBCA participating in the synthesis of poly-γ-glutamate derived from a *Bacillus* sp. strain and a Gram-negative bacterium as the host cell.

To introduce the lipase gene to the surface expression vector pGNA using a Gram-negative bacterium as the host cell, about 0.5 kb of the lipase gene was cloned into the general cloning vector pUC8 and utilized as the template and oligonucleotides containing the nucleotide sequences of SEQ ID NO: 28 and SEQ ID NO: 29 used as the primers for performing a polymerase chain reaction. At this point, the amplified region of the genes was 546 bp in size. The primers with SEQ ID NO: 28 and SEQ ID NO: 29 were also constructed to include the restriction enzyme BamHI and HindIII recognition sites present in the surface expression vector pGNA.

The amplified L gene of the hepatitis B virus was digested with the restriction enzymes HindIII and BamHI and ligated to the C-terminal region of the cell outer membrane gene participating in the synthesis of poly-γ-glutamate by adjusting the translation codons. The recombinant expression vector pGNA-lipase constructed above is depicted in FIG. 22.

(2) The surface expression of the lipase gene in *E. coli* was investigated using the recombinant expression vector pGNA-lipase. For this purpose, the expression vector pGNA-lipase was transformed into *E. coli* and expression induced through the same procedure as described in Example 3. Thereafter, the enzymatic activity of the lipase expressed onto the cell surface was assayed on an agar medium (1% Trypton, 0.5% yeast extract, 0.619% NaCl, 0.5% gum Arabic, 1 mM CaCl, 1% Tricaprylin) containing 1% of Tricaprylin with oil degradation activity. The *E. coli* transformant was smeared onto the agar medium containing 1% of an oil substrate, then cultivated in a sustained state at 37° C. for 9 hours.

As a result, the degradation of the oil substrate changed to clear regions (See FIG. 22), thereby confirming the surface expression of the lipase onto the cell surface.

Example 22

Construction of Recombinant Surface Expression Vector pGNA-amidase and Surface Expression of Amidase (1) The recombinant expression vector pGNA-amidase that can express the amidase enzyme onto a cell surface was constructed using the pgsA gene from the cell outer membrane protein gene pgsBCA participating in the synthesis of poly-γ-glutamate derived from a *Bacillus* sp. strain and a Gram-negative bacterium as the host cell.

To introduce the amidase gene to the surface expression vector pGNA using a Gram-negative bacterium as the host cell, about 0.8 kb of the amidase gene was cloned into the *E. coli* expression vector pGNA and utilized as the template and oligonucleotides containing the nucleotide sequences of SEQ ID NO: 30 and SEQ ID NO: 31 used as the primers for a polymerase chain reaction. At this point, the amplified region of the genes was 792 bp in size. The primers with SEQ ID NO: 30 and SEQ ID NO: 31 were also constructed to include the restriction enzyme BamHI and HindIII recognition sites present in the surface expression vector pGNA.

The amplified L gene of the hepatitis B virus was digested with the restriction enzymes HindIII and BamHI and ligated to the surface expression vector pGNA in the C-terminal region of the cell outer membrane gene participating in the synthesis of poly-γ-glutamate by adjusting the translation codons. The recombinant expression vector pGNA-amidse constructed above is depicted in FIG. 23.

(2) The surface expression of the amidase gene in *E. coli* was investigated using the recombinant expression vector pGNA-amidase. For this purpose, the expression vector pGNA-amidase was transformed into *E. coli* and expression induced through the same procedure as described for Example 3. Thereafter, the enzymatic activity of the amidase expressed onto the cell surface was assayed by adding the *E. coli* to 100 mM of a Tris-HCl buffer solution (pH 8.0) containing 10 mM of D-alaNH as a substrate and 0.5 mM of CoCl as a cofactor. In detail, the *E. coli* on which the amidase had been expressed was examined using HPLC (Hypersil ODS; 250×4.6 mm column) after reacting for some hours and the OD value at 600 nm for cell growth was 1 as a unit volume. At this point, wild type *E. coli* and the cell transformant containing the surface expression vector pGNA were utilized to compare the enzymatic activities of the amidase expressed onto the cell surface.

As illustrated in FIG. 23, the *E. coli* transformant of the present invention was found to exhibit 100-fold more amidase activity than the control group. Therefore, the method for surface expression in the current invention was confirmed to effectively express amidase onto the cell surface.

INDUSTRIAL APPLICABILITY

As demonstrated and confirmed above, the novel expression vectors of the present invention can efficiently produce an exogenous protein on a microbial surface by exploiting the cell outer membrane protein (pgsBCA) participating in the synthesis of poly-γ-glutamate derived from a *Bacillus* sp. as a surface expression carrier and can be stably applied to both Gram-negative and Gram-positive bacterium. The cell transformant transformed with the surface expression vector includes an insertion site for the targeted exogenous protein, then ligating foreign genes encoding the exogenous protein are prepared and cultivated to facilitate the cell surface expression.

The surface expression vectors of the present invention can be effectively used for the stable and easily detectable surface expression of various exogenous proteins onto a cell surface regardless of the cell cycle. Consequently, the proposed microbial surface expression system can be utilized to produce various antigens, recombinant antibodies, recombinant enzymes, and attachment or adsorption proteins, screening various antigens and antibodies, and producing enzymes for biological conversion. Essentially, the enzymes can be expressed onto a cell surface and used without any reduction in the catalyst activity, thereby allowing the present invention to be industrially applied for the purpose of bioconversion.

Those skilled in the art will appreciate that the concepts and specific embodiments disclosed in the foregoing description can be readily utilized as a basis for modifying or designing other embodiments for carrying out the same purposes as the current invention.

Those skilled in the art will also appreciate that such equivalent embodiments do not depart from the spirit and scope of the present invention as set forth in the appended claims.

What is claimed is:

1. An expression vector for producing a target protein on a microbial cell surface, which contains one or more genes selected from the group consisting of pgsB, pgsC and pgsA, encoding a poly-γ-glutamate synthetase complex and a gene encoding a target protein, wherein the nucleotide sequences of pgsB, pgsC and pgsA genes comprises SEQ ID NO: 1, SEQ ID NO: 2, and SEQ ID NO: 3, respectively.

2. The expression vector for producing a target protein on a microbial cell surface according to claim 1, in which said pgsB, pgsC and pgsA genes are isolated from a *Bacillus* sp. strain producing poly-γ-glutamate synthetase.

3. The expression vector for producing a target protein on a microbial cell surface according to claim 1, in which said gene encoding the target protein can be selected from genes encoding enzymes, antigens, antibodies, attachment proteins, or adsorption proteins.

4. The expression vector for producing a target protein on a microbial cell surface according to claim 1, in which said expression vector is utilized for Gram-negative bacteria.

5. The Gram-negative bacterium that is transformed with the expression vector for producing a target protein on a microbial cell surface as in claim 4.

6. The expression vector for producing a target protein on a microbial cell surface according to claim 1, in which said expression vector is utilized for Gram-positive bacteria.

7. The Gram-positive bacterium that is transformed with the expression vector for producing a target protein on a microbial cell surface as in claim 6.

8. The expression vector for producing a target protein on a microbial cell surface according to claim 1, in which said expression vector can be utilized for both Gram-negative and Gram-positive bacteria.

9. A method for expressing a target protein on the microbial cell surface said method comprising:

cultivating the transformed Gram-negative bacteria of claim 5.

10. A method for expressing a target protein on the microbial cell surface said method comprising:

cultivating the transformed Gram-positive bacteria of claim 7.

11. An expression vector for producing a target protein on a microbial cell surface, which contains one or more genes selected from the group consisting of pgsB, pgsC and pgsA, encoding a poly-γ-glutamate synthetase complex and a gene encoding a target protein, wherein said pgsB, pgsC and pgsA genes are isolated from a *Bacillus* sp. strain producing poly-γ-glutamate synthetase.

* * * * *

SEQUENCE LISTING

<160> NUMBER OF SEQ ID NOS: 8

<210> SEQ ID NO 1
<211> LENGTH: 1182
<212> TYPE: DNA
<213> ORGANISM: Bacillus subtilis

<400> SEQUENCE: 1

| | | | | | |
|---|---|---|---|---|---:|
| atgggctggt | tactcattat | agcctgtgct | gtcatactgg | tcatcggaat | attagaaaaa | 60 |
| cgacgacatc | agaaaaacat | tgatgccctc | cctgttcggg | tgaatattaa | cggcatccgc | 120 |
| ggaaaatcga | ctgtgacaag | gctgacaacc | ggaatattaa | tagaagccgg | ttacaagact | 180 |
| gttggaaaaa | caacaggaac | agatgcaaga | atgatttact | gggacacacc | ggaggaaaag | 240 |
| ccgattaaac | ggaaacctca | ggggccgaat | atcggagagc | aaaaagaagt | catgagagaa | 300 |
| acagtagaaa | gaggggctaa | cgcgattgtc | agtgaatgca | tggctgttaa | cccagattat | 360 |
| caaatcatct | ttcaggaaga | acttctgcag | gccaatatcg | gcgtcattgt | gaatgtttta | 420 |
| gaagaccata | tggatgtcat | ggggccgacg | cttgatgaaa | ttgcagaagc | gtttaccgct | 480 |
| acaattcctt | ataatggcca | tcttgtcatt | acagatagtg | aatataccga | gttctttaaa | 540 |
| caaaaagcaa | agaacgaaa | cacaaaagtc | atcattgctg | ataactcaaa | aattacagat | 600 |
| gagtatttac | gtaattttga | atacatggta | ttccctgata | acgcttctct | ggcgctgggt | 660 |
| gtggctcaag | cactcggcat | tgacgaagaa | acagcattta | agggaatgct | gaatgcgccg | 720 |
| ccagatccgg | gagcaatgag | aattcttccg | ctgatcagtc | cgagcgagcc | tgggcacttt | 780 |
| gttaatgggt | ttgccgcaaa | cgacgcttct | tctactttga | atatatggaa | acgtgtaaaa | 840 |
| gaaatcggtt | acccgaccga | tgatccgatc | atcatcatga | actgccgcgc | agaccgtgtc | 900 |
| gatcggacac | agcaattcgc | aaatgacgta | ttgccttata | ttgaagcaag | tgaactgatc | 960 |
| ttaatcggtg | aaacaacaga | accgatcgta | aaagcctatg | aagaaggcaa | aattcctgca | 1020 |
| gacaaactgc | atgacctaga | gtataagtca | acagatgaaa | ttatggaatt | gttaaagaaa | 1080 |
| agaatgcaca | accgtgtcat | atatggcgtc | ggcaatattc | atggtgccgc | agagcccttta | 1140 |
| attgaaaaaa | tccacgaata | caaggtaaag | cagctcgtaa | gc | | 1182 |

<210> SEQ ID NO 2
<211> LENGTH: 447
<212> TYPE: DNA
<213> ORGANISM: Bacillus subtilis

<400> SEQUENCE: 2

| | | | | | |
|---|---|---|---|---|---:|
| atgttcggat | cagatttata | catcgcacta | attttaggtg | tactactcag | tttaattttt | 60 |
| gcggaaaaaa | cagggatcgt | gccggcagga | cttgttgtac | cgggatattt | aggacttgtg | 120 |
| tttaatcagc | cggtctttat | tttacttgtt | ttgctagtga | gcttgctcac | ttatgttatc | 180 |
| gtgaaatacg | gttatccaa | atttatgatt | ttgtacggac | gcagaaaatt | cgctgccatg | 240 |
| ctgataacag | ggatcgtcct | aaaaatcgcg | tttgattttc | tatacccgat | tgtaccattt | 300 |
| gaaatcgcag | aatttcgagg | aatcggcatc | atcgtgccag | gtttaattgc | caataccatt | 360 |
| cagaaacaag | gtttaaccat | tacgttcgga | agcacgctgc | tattgagcgg | agcgaccttt | 420 |
| gctatcatgt | ttgtttacta | cttaatt | | | | 447 |

<210> SEQ ID NO 3
<211> LENGTH: 1140

```
<212> TYPE: DNA
<213> ORGANISM: Bacillus subtilis

<400> SEQUENCE: 3
atgaaaaaag aactgagctt tcatgaaaag ctgctaaagc tgacaaaaca gcaaaaaaag      60
aaaaccaata agcacgtatt tattgccatt ccgatcgttt ttgtccttat gttcgctttc     120
atgtgggcgg aaaagcgga aacgccgaag gtcaaaacgt attctgacga cgtactctca     180
gcctcatttg taggcgatat tatgatggga cgctatgttg aaaaagtaac ggagcaaaaa     240
ggggcagaca gtattttca atatgttgaa ccgatcttta gagcctcgga ttatgtagca     300
ggaaactttg aaaacccggt aacctatcaa agaattata acaagcaga taagagatt      360 catctgcaga cgaataagga atcagtgaaa gtcttgaagg atatgaattt cacggttctc     420
aacagcgcca acaaccacgc aatggattac ggcgttcagg gcatgaaaga tacgcttgga     480
gaatttgcga agcaaaacct tgatatcgtt ggagcgggat acagcttaag tgatgcgaaa     540
aagaaaattt cgtaccagaa agtcaacggg gtaacgattg caacgcttgg ctttaccgat     600
gtgtccggga aaggtttcgc ggctaaaaag aatacgccgg gcgtgctgcc cgcagatcct     660
gaaatcttca tccctatgat ttcagaagcg aaaaaacatg ctgacattgt tgttgtgcag     720
tcacactggg gccaagagta tgacaatgat ccaaacgacc gccagcgcca gcttgcaaga     780
gccatgtctg atgcgggagc tgacatcatc gtcggccatc atccgcacgt cttagaaccg     840
attgaagtat ataacggaac cgtcattttc tacagcctcg gcaactttgt ctttgaccaa     900
ggctggacga gaacaagaga cagtgcactg gttcagtatc acctgaagaa aaatggaaca     960
ggccgctttg aagtgacacc gatcgatatc catgaagcga cacctgcacc tgtgaaaaaa    1020
gacagcctta aacagaaaac cattattcgc gaactgacga aagactctaa tttcgcttgg    1080
aaagtagaag acggaaaact gacgtttgat attgatcata gtgacaaact aaaatctaaa    1140

<210> SEQ ID NO 4
<211> LENGTH: 31
<212> TYPE: DNA
<213> ORGANISM: Artificial Sequence
<220> FEATURE:
<223> OTHER INFORMATION: Synthetic Construct

<400> SEQUENCE: 4
gaaccatggg ctggttactc cttatagcct g                                    31

<210> SEQ ID NO 5
<211> LENGTH: 30
<212> TYPE: DNA
<213> ORGANISM: Artificial Sequence
<220> FEATURE:
<223> OTHER INFORMATION: Synthetic Construct

<400> SEQUENCE: 5
ctcggatcct ttagatttta gtttgtcact                                      30

<210> SEQ ID NO 6
<211> LENGTH: 6536
<212> TYPE: DNA
<213> ORGANISM: Artificial Sequence
<220> FEATURE:
<223> OTHER INFORMATION: Synthetic Construct

<400> SEQUENCE: 6
gatctctcct tcacagattc ccaatctctt gttaaataac gaaaaagcat caatcaaaac      60
```

-continued

| | | | | |
|---|---|---|---|---|
| ggcggcatgt | ctttctatat | tccagcaatg | ttttatagggg | gacatattga | tgaagatggg | 120 |
| tatcacctta | gtaaaaaaag | aattgctata | agctgctctt | ttttgttcgt | gatatactga | 180 |
| taataaattg | aattttcaca | cttctggaaa | aaggagatat | accatgggct | ggttactcat | 240 |
| tatagcctgt | gctgtcatac | tggtcatcgg | aatattagaa | aaacgacgac | atcagaaaaa | 300 |
| cattgatgcc | ctccctgttc | gggtgaatat | taacggcatc | cgcggaaaat | cgactgtgac | 360 |
| aaggctgaca | accggaatat | aatagaagc | cggttacaag | actgttggaa | aaacaacagg | 420 |
| aacagatgca | agaatgattt | actgggacac | accggaggaa | aagccgatta | acggaaacc | 480 |
| tcaggggccg | aatatcggag | agcaaaaaga | agtcatgaga | gaaacagtag | aaagaggggc | 540 |
| taacgcgatt | gtcagtgaat | gcatggctgt | taacccagat | tatcaaatca | tctttcagga | 600 |
| agaacttctg | caggccaata | tcggcgtcat | tgtgaatgtt | ttagaagacc | atatggatgt | 660 |
| catggggccg | acgcttgatg | aaattgcaga | agcgtttacc | gctacaattc | cttataatgg | 720 |
| ccatcttgtc | attacagata | gtgaatatac | cgagttcttt | aaacaaaaag | caaagaacg | 780 |
| aaacacaaaa | gtcatcattg | ctgataactc | aaaaattaca | gatgagtatt | tacgtaattt | 840 |
| tgaatacatg | gtattccctg | ataacgcttc | tctggcgctg | ggtgtggctc | aagcactcgg | 900 |
| cattgacgaa | gaaacagcat | ttaagggaat | gctgaatgcg | ccgccagatc | cgggagcaat | 960 |
| gagaattctt | ccgctgatca | gtccgagcga | gcctgggcac | tttgttaatg | ggtttgccgc | 1020 |
| aaacgacgct | tcttctactt | tgaatatatg | gaaacgtgta | aaagaaatcg | gttacccgac | 1080 |
| cgatgatccg | atcatcatca | tgaactgccg | cgcagaccgt | gtcgatcgga | cacagcaatt | 1140 |
| cgcaaatgac | gtattgcctt | atattgaagc | aagtgaactg | atcttaatcg | gtgaaacaac | 1200 |
| agaaccgatc | gtaaaagcct | atgaagaagg | caaaattcct | gcagacaaac | tgcatgacct | 1260 |
| agagtataag | tcaacagatg | aaattatgga | attgttaaag | aaaagaatgc | acaaccgtgt | 1320 |
| catatatggc | gtcggcaata | ttcatggtgc | cgcagagcct | ttaattgaaa | aaatccacga | 1380 |
| atacaaggta | aagcagctcg | taagctaggg | ggaaatgcaa | acatgttcgg | atcagattta | 1440 |
| tacatcgcac | taattttagg | tgtactactc | agtttaattt | ttgcggaaaa | acagggatc | 1500 |
| gtgccggcag | gacttgttgt | accgggatat | ttaggacttg | tgtttaatca | gccggtcttt | 1560 |
| attttacttg | ttttgctagt | gagcttgctc | acttatgtta | tcgtgaaaata | cggtttatcc | 1620 |
| aaatttatga | ttttgtacgg | acgcagaaaa | ttcgctgcca | tgctgataac | agggatcgtc | 1680 |
| ctaaaaatcg | cgtttgattt | tctatacccg | attgtaccat | ttgaaatcgc | agaatttcga | 1740 |
| ggaatcggca | tcatcgtgcc | aggtttaatt | gccaatacca | ttcagaaaca | aggtttaacc | 1800 |
| attacgttcg | gaagcacgct | gctattgagc | ggagcgacct | ttgctatcat | gtttgtttac | 1860 |
| tacttaattt | aatgtaaggt | gtgtcaaacg | atgaaaaaag | aactgagctt | tcatgaaaag | 1920 |
| ctgctaaagc | tgacaaaaca | gcaaaaaaag | aaaaccaata | agcacgtatt | tattgccatt | 1980 |
| ccgatcgttt | ttgtccttat | gttcgctttc | atgtgggcgg | gaaaagcgga | aacgccgaag | 2040 |
| gtcaaaacgt | attctgacga | cgtactctca | gcctcatttg | taggcgatat | tatgatggga | 2100 |
| cgctatgttg | aaaaagtaac | ggagcaaaaa | ggggcagaca | gtattttca | atatgttgaa | 2160 |
| ccgatcttta | gagcctcgga | ttatgtagca | ggaaactttg | aaaacccggt | aacctatcaa | 2220 |
| aagaattata | aacaagcaga | taagagatt | catctgcaga | cgaataagga | atcagtgaaa | 2280 |
| gtcttgaagg | atatgaattt | cacggttctc | aacagcgcca | acaaccacgc | aatggattac | 2340 |
| ggcgttcagg | gcatgaaaga | tacgcttgga | gaatttgcga | agcaaaacct | tgatatcgtt | 2400 |
| ggagcgggat | acagcttaag | tgatgcgaaa | aagaaaattt | cgtaccagaa | agtcaacggg | 2460 |

-continued

```
gtaacgattg caacgcttgg ctttaccgat gtgtccggga aaggtttcgc ggctaaaaag   2520
aatacgccgg gcgtgctgcc cgcagatcct gaaatcttca tccctatgat ttcagaagcg   2580
aaaaaacatg ctgacattgt tgttgtgcag tcacactggg gccaagagta tgacaatgat   2640
ccaaacgacc gccagcgcca gcttgcaaga gccatgtctg atgcgggagc tgacatcatc   2700
gtcggccatc atccgcacgt cttagaaccg attgaagtat ataacggaac cgtcattttc   2760
tacagcctcg gcaactttgt ctttgaccaa ggctggacga gaacaagaga cagtgcactg   2820
gttcagtatc acctgaagaa aaatggaaca ggccgctttg aagtgacacc gatcgatatc   2880
catgaagcga cacctgcacc tgtgaaaaaa gacagcctta aacagaaaac cattattcgc   2940
gaactgacga aagactctaa tttcgcttgg aaagtagaag acggaaaact gacgtttgat   3000
attgatcata gtgacaaact aaaatctaaa ggatcctcta gagtcgacct gcaggcatgc   3060
aagcttggct gttttggcgg atgagagaag attttcagcc tgatacagat taaatcagaa   3120
cgcagaagcg gtctgataaa acagaatttg cctggcggca gtagcgcggt ggtcccacct   3180
gaccccatgc cgaactcaga agtgaaacgc cgtagcgccg atggtagtgt ggggtctccc   3240
catgcgagag tagggaactg ccaggcatca aataaaacga aaggctcagt cgaaagactg   3300
ggcctttcgt tttatctgtt gtttgtcggt gaacgctctc ctgagtagga caaatccgcc   3360
gggagcggat ttgaacgttg cgaagcaacg gcccggaggg tggcgggcag gacgcccgcc   3420
ataaactgcc aggcatcaaa ttaagcagaa ggccatcctg acggatggcc ttttgcgtt    3480 tctacaaact cttttgttt atttttctaa atacattcaa atatgtatcc gctcatgaga   3540
caataaccct gataaatgct tcaataatat tgaaaaagga agagtatgag tattcaacat   3600
ttccgtgtcg cccttattcc cttttttgcg gcattttgcc ttcctgtttt tgctcaccca   3660
gaaacgctgg tgaaagtaaa agatgctgaa gatcagttgg gtgcacgagt gggttacatc   3720
gaactggatc tcaacagcgg taagatcctt gagagttttc gccccgaaga acgttttcca   3780
atgatgagca cttttaaagt tctgctatgt ggcgcggtat tatcccgtgt tgacgccggg   3840
caagagcaac tcggtcgccg catacactat tctcagaatg acttggttga gtaattcact   3900
ggccgtcgtt ttacaacgtc gtgactggga aaaccctggc gttacccaac ttaatcgcct   3960
tgcagcacat ccccctttcg ccagctggcg taatagcgaa gaggcccgca ccgatcgccc   4020
ttcccaacag ttgcgcagcc tgaatggcga atggcgcctg atgcggtatt ttctccttac   4080
gcatctgtgc ggtatttcac accgcatatg gtgcactctc agtacaatct gctctgatgc   4140
cgcatagtta agccagcccc gacacccgcc aacacccgct gacgcgccct gacgggcttg   4200
tctgctcccg gcatccgctt acagacaagc tgtgaccgtc tccggagct gcatgtgtca    4260 gaggttttca ccgtcatcac cgaaacgcgc gagacgaaag gcctcgtga tacgcctatt    4320 tttataggtt aatgtcatga taataatggt ttcttagacg tcaggtggca cttttcgggg   4380
aaatgtgcgc ggaaccccta tttgtttatt tttctaaata cattcaaata tgtatccgct   4440
catgagacaa taaccctgat aaatgcttca ataatattga aaaggaaga gtatgagtat    4500 tcaacatttc cgtgtcgccc ttattccctt ttttgcggca ttttgccttc ctgtttttgc    4560
tcacccagaa acgctggtga agtaaaaga tgctgaagat cagttgggtg cacgagtggg    4620
ttacatcgaa ctggatctca acagcggtaa gatccttgag agttttcgcc ccgaagaacg    4680
ttttccaatg atgagcactt ttaaagttct gctatgtggc gcggtattat cccgtattga    4740
cgccgggcaa gagcaactcg gtcgccgcat acactattct cagaatgact tggttgagta    4800
```

-continued

```
ctcaccagtc acagaaaagc atcttacgga tggcatgaca gtaagagaat tatgcagtgc    4860
tgccataacc atgagtgata acactgcggc caacttactt ctgacaacga tcggaggacc    4920
gaaggagcta accgcttttt tgcacaacat gggggatcat gtaactcgcc ttgatcgttg    4980
ggaaccggag ctgaatgaag ccataccaaa cgacgagcgt gacaccacga tgcctgtagc    5040
aatggcaaca acgttgcgca aactattaac tggcgaacta cttactctag cttcccggca    5100
acaattaata gactggatgg aggcggataa agttgcagga ccacttctgc gctcggccct    5160
tccggctggc tggtttattg ctgataaatc tggagccggt gagcgtgggt ctcgcggtat    5220
cattgcagca ctggggccag atggtaagcc ctcccgtatc gtagttatct acacgacggg    5280
gagtcaggca actatggatg aacgaaatag acagatcgct gagataggtg cctcactgat    5340
taagcattgg taactgtcag accaagttta ctcatatata ctttagattg atttaaaact    5400 tcattttttaa tttaaaagga tctaggtgaa gatcctttt gataatctca tgaccaaaat    5460
cccttaacgt gagttttcgt tccactgagc gtcagacccc gtagaaaaga tcaaaggatc    5520
ttcttgagat cctttttttc tgcgcgtaat ctgctgcttg caaacaaaaa aaccaccgct    5580
accagcggtg gtttgtttgc cggatcaaga gctaccaact cttttttccga aggtaactgg    5640 cttcagcaga gcgcagatac caaatactgt ccttctagtg tagccgtagt taggccacca    5700
cttcaagaac tctgtagcac cgcctacata cctcgctctg ctaatcctgt taccagtggc    5760
tgctgccagt ggcgataagt cgtgtcttac cgggttggac tcaagacgat agttaccgga    5820
taaggcgcag cggtcgggct gaacgggggg ttcgtgcaca cagcccagct tggagcgaac    5880
gacctacacc gaactgagat acctacagcg tgagcattga gaaagcgcca cgcttcccga    5940
agggagaaag gcggacaggt atccggtaag cggcagggtc ggaacaggag agcgcacgag    6000
ggagcttcca gggggaaacg cctggtatct ttatagtcct gtcgggtttc gccacctctg    6060
acttgagcgt cgatttttgt gatgctcgtc aggggggcgg agcctatgga aaaacgccag    6120
caacgcggcc tttttacggt tcctggcctt ttgctggcct tttgctcaca tgttctttcc    6180
tgcgttatcc cctgattctg tggataaccg tattaccgcc tttgagtgag ctgataccgc    6240
tcgccgcagc cgaacgaccg agcgcagcga gtcagtgagc gaggaagcgg aagagcgccc    6300
aatacgcaaa ccgcctctcc ccgcgcgttg gccgattcat taatgcagct ggcacgacag    6360
gtttcccgac tggaaagcgg gcagtgagcg caacgcaatt aatgtgagtt agctcactca    6420
ttaggcaccc caggctttac actttatgct tccggctcgt atgttgtgtg gaattgtgag    6480
cggataacaa tttcacacag gaaacagcta tgaccatgat tacgccaagc tagctt       6536
```

<210> SEQ ID NO 7
<211> LENGTH: 29
<212> TYPE: DNA
<213> ORGANISM: Artificial Sequence
<220> FEATURE:
<223> OTHER INFORMATION: Synthetic Construct

<400> SEQUENCE: 7

```
ctgggatccc aaggtatgtt gcccgtttg                                         29
```

<210> SEQ ID NO 8
<211> LENGTH: 30
<212> TYPE: DNA
<213> ORGANISM: Artificial Sequence
<220> FEATURE:

```
<223> OTHER INFORMATION: Synthetic Construct

<400> SEQUENCE: 8
tgaagcttat taggacgatg ggatgggaat                                            30
```